United States Patent
Caciula et al.

(10) Patent No.: US 9,908,097 B2
(45) Date of Patent: *Mar. 6, 2018

(54) CONTROLLABILITY OXIDATIVE DEHYDROGENATION PROCESS FOR PRODUCING BUTADIENE

(71) Applicant: TPC Group LLC, Houston, TX (US)

(72) Inventors: Liana Caciula, Houston, TX (US);
Joseph G. Duff, League City, TX (US);
Sirisha Chada, Houston, TX (US);
Elizabeth Ballard, Houston, TX (US);
Cecil G. McFarland, League City, TX (US)

(73) Assignee: TPC GROUP LLC, Houston, TX (US)

( * ) Notice: Subject to any disclaimer, the term of this patent is extended or adjusted under 35 U.S.C. 154(b) by 132 days.

This patent is subject to a terminal disclaimer.

(21) Appl. No.: 14/386,550

(22) PCT Filed: Mar. 28, 2013

(86) PCT No.: PCT/US2013/034215
§ 371 (c)(1),
(2) Date: Sep. 19, 2014

(87) PCT Pub. No.: WO2013/148913
PCT Pub. Date: Oct. 3, 2013

(65) Prior Publication Data
US 2015/0073184 A1      Mar. 12, 2015

Related U.S. Application Data

(60) Provisional application No. 61/617,535, filed on Mar. 29, 2012, provisional application No. 61/617,506, filed on Mar. 29, 2012.

(51) Int. Cl.
*C07C 5/09* (2006.01)
*C07C 5/48* (2006.01)
(Continued)

(52) U.S. Cl.
CPC ............ *B01J 19/24* (2013.01); *C07C 5/09* (2013.01); *C07C 5/48* (2013.01); *C07C 7/005* (2013.01);
(Continued)

(58) Field of Classification Search
CPC .. C07C 5/48; C07C 7/005; C07C 5/09; C07C 2527/185; C07C 2523/80;
(Continued)

(56) References Cited

U.S. PATENT DOCUMENTS 2,444,035 A * 6/1948 Corson .................. B01J 21/16
                                                    502/174
3,284,536 A    11/1966 Bajars
(Continued)

FOREIGN PATENT DOCUMENTS

| CN | 101674883 A | 3/2010 |
| CN | 101980992 A | 2/2011 |

(Continued)

OTHER PUBLICATIONS

Welch, et al., "Butadiene Via Oxidative Dehydrogenation", Hydrocarbon Processing, Nov. 1978, pp. 131-136.
European Search Report and Written Opinion dated Nov. 6, 2015.

*Primary Examiner* — Philip Louie
*Assistant Examiner* — Aaron Pierpont
(74) *Attorney, Agent, or Firm* — Michael W. Ferrell; Roberts S. Alexander; Ferrells, PLLC

(57) ABSTRACT

Butadiene is made from a butene rich feed by passing a superheated butene rich feed including superheated steam and oxygen at a temperature of at least about 343° C. (650° F.) over a catalyst bed having a depth of over about 69 cm (27 inches) of granules of ferritic oxidative dehydrogenation catalyst. Inlet conditions being controlled such that the oxidative dehydrogenation reactions initially occur in the
(Continued)

lower most layers of catalyst. Process control includes monitoring the temperature throughout the bed and increasing the inlet temperature in response to a drop in the temperature in the active layer, when the active layer of oxidative dehydrogenation catalyst begins to become deactivated so that the reaction zone moves upwardly in the oxidative dehydrogenation bed.

20 Claims, 8 Drawing Sheets

(51) Int. Cl.
| | | |
|---|---|---|
| B01J 19/24 | (2006.01) | |
| C07C 7/00 | (2006.01) | |
| B01J 23/889 | (2006.01) | |
| B01J 27/187 | (2006.01) | |

(52) U.S. Cl.
CPC .......... *B01J 23/8892* (2013.01); *B01J 27/187* (2013.01); *B01J 2219/00103* (2013.01); *B01J 2219/24* (2013.01); *B01J 2523/00* (2013.01); *C07C 2523/745* (2013.01); *C07C 2523/80* (2013.01); *C07C 2527/185* (2013.01)

(58) Field of Classification Search
CPC ............. C07C 2523/745; B01J 19/0013; B01J 2219/00051; B01J 2219/00063
USPC ............. 585/254, 315, 501, 601, 602; 502/6
See application file for complete search history.

(56) References Cited

U.S. PATENT DOCUMENTS

| | | | |
|---|---|---|---|
| 3,496,070 A | 2/1970 | Woerner et al. | |
| 3,849,511 A * | 11/1974 | Manning | B01J 23/862 585/433 |
| 3,887,631 A | 6/1975 | Yaffe | |
| 3,925,498 A | 12/1975 | Stadig | |
| 3,943,185 A | 3/1976 | Tschopp | |
| 3,953,370 A | 4/1976 | Miklas | |
| 4,083,884 A * | 4/1978 | Purdy | C07C 5/48 502/329 |
| 4,150,063 A | 4/1979 | Besozzi et al. | |
| 4,266,086 A | 5/1981 | Patel | |
| 4,595,788 A | 6/1986 | Yamamoto et al. | |
| 4,644,088 A * | 2/1987 | McFarland | B01J 23/755 585/624 |
| 4,658,080 A | 4/1987 | McFarland | |
| 4,975,407 A | 12/1990 | Dejaifve et al. | |
| 5,139,988 A | 8/1992 | Sasaki et al. | |
| 5,772,898 A | 6/1998 | Lewis | |
| 2004/0122268 A1 | 6/2004 | Van Egmond | |
| 2004/0122275 A1 | 6/2004 | Levin et al. | |
| 2007/0299278 A1 * | 12/2007 | Hechler | B01J 8/067 560/214 |
| 2008/0183024 A1 * | 7/2008 | Klanner | C07C 5/3337 585/633 |
| 2009/0318741 A1 * | 12/2009 | Newman | C07B 35/04 585/440 |
| 2010/0121123 A1 | 5/2010 | Chung et al. | |
| 2011/0004041 A1 | 1/2011 | Chung et al. | |
| 2011/0245568 A1 | 10/2011 | Khabashesku et al. | |
| 2015/0080627 A1 | 3/2015 | Caciula et al. | |

FOREIGN PATENT DOCUMENTS

| | | |
|---|---|---|
| CN | 104507894 A | 4/2015 |
| EP | 2256101 A2 | 12/2010 |
| FR | 2093792 A5 | 1/1972 |
| FR | 244019 A1 | 7/1980 |
| JP | 2010105983 A | 5/2010 |
| WO | 2002022258 A2 | 3/2002 |
| WO | 2012011659 A2 | 1/2012 |

* cited by examiner

CONTROLLABILITY OXIDATIVE DEHYDROGENATION PROCESS FOR PRODUCING BUTADIENE

CROSS-REFERENCE TO RELATED APPLICATION(S)

This National Phase Application is based on International Application No. PCT/US2013/034215 of the same title filed Mar. 28, 2013, the priority of which is hereby claimed and the disclosure of which is incorporated herein by reference.

BACKGROUND

Previously known processes for producing butadiene from butene rich hydrocarbonaceous feeds have used reactors whose shapes were largely governed by pressure drop considerations leading to reactors that would be considered shallow—the bed depth (linear dimension in the direction of flow) of all four layers of the bed often being limited to about a meter or less with the total height of the oxidative dehydrogenation catalyst being only about 55-60 cm (22-24 inches) or less. In particular, previous processes typically used natural gas to vaporize butene and heat a mixture of hydrocarbons, preferably butenes, oxygen and steam to a temperature in excess of 260° C. (500° F.), more commonly in excess of about 315° C. (600° F.), and preferably over about 345° C. (650° F.) or, in some cases, even over 370° C. (700° F.). In a typical process, the reaction mixture includes butenes, oxygen in an amount of from about 0.4 moles to about 0.8 moles, more typically from slightly in excess of 0.5 moles up to about 0.65 moles of oxygen for each mole of butene in the butene rich hydrocarbonaceous feed, and superheated steam in amounts of from about 12:1 to about 16:1. The heated reaction mixture was passed over a multilayer bed comprising four layers: an inert flow distribution and catalyst retention layer which restricted channeling of the reaction mixture as it passed through the catalyst bed and also served to hold the lower layers in place against vorticity that might be present above the catalyst bed; the second layer comprising the bulk of the bed was an oxidation/dehydrogenation catalyst; while the third layer comprises an aldehyde and alkyne removal ("AAR") catalyst which converts alkynes and aldehydes in the product into compounds which are less detrimental to processes for polymerization of butadienes than alkynes and aldehydes. The lowest layer comprises an inert particulate support material. As mentioned typically, the total bed height would be limited to about a meter or less while the depth of the oxidative dehydrogenation layer was limited to less than about 56 cm (22 inches).

While passing over the oxidation/dehydrogenation catalyst, the butenes were converted to butadiene accompanied by the liberation of a great deal of heat, resulting in temperatures in the neighborhood of 540° C. or 595° C. (1000° F. or 1100° F.). In the past, when the depth of the catalyst bed was shallow, breakthrough of oxygen to the AAR catalyst could be difficult to prevent even though care might typically be exercised to ensure that all of the oxygen present in the reaction mixture was consumed before reaching the AAR catalyst. Oxygen breakthrough can lead to both loss of the desired butadiene product and, even more seriously, damage to the AAR catalyst and/or reactor vessel. Consequently, in many cases, these considerations led to use of rather conservative cycle length and premature catalyst changeout, so that the effective catalyst life was shorter than necessary and percentage of time on-stream suffered.

Subsequent to reaction, the reaction product mixture is cooled and butadiene separated by contact with absorber oil and subsequent fractionation. Typically, these processes produce crude butadiene at a purity ranging from about 50 to about 70%, more typically from about 55 to about 65%, which is passed onward in the plant for further processing using known technologies.

References of interest are discussed below.

Lewis; HYDROCARBON CONVERSION PROCESS USING NOVEL METALLO MANGANESE OXIDES; U.S. Pat. No. 5,772,898; Jun. 30, 1998; relates to a hydrocarbon conversion process comprising contacting a hydrocarbon feed with a catalyst comprising a crystalline metallo manganese oxide composition having a three-dimensional framework structure, an intracrystalline pore system and an empirical chemical composition on an anhydrous basis expressed by the formula:

$$A_y Mn_{8-x} M_x O_{16}$$

where A is a templating agent selected from alkali metals, alkaline earth metals and ammonium ion, "y" is the moles of A and varies from the group consisting of about 0.5 to about 2.0, M is a metal selected from the group consisting of chromium, zirconium, tin, platinum, rhodium, niobium, tantalum, vanadium, antimony, ruthenium, gallium and germanium, "x" is the moles of M and varies from about 0.01 to about 4.0 and is characterized in that manganese has a valence of +3, or +4, M has a valence of +3, +4 or +5 and the composition has the hollandite structure.

Sasaki et al.; IRON-ANTIMONY-CONTAINING METAL OXIDE CATALYST COMPOSITION AND PROCESS FOR PRODUCING THE SAME; U.S. Pat. No. 5,139,988; Aug. 18, 1992; relates to a composition which contains as essential components: crystalline iron antimonate and at least one element selected from the group consisting of vanadium, molybdenum, and tungsten; is useful as a catalyst in the oxidation reaction of organic compounds. Also, a process for producing the composition is disclosed.

Dejaifve et al.; CATALYST FOR DEHYDROGENATING ORGANIC COMPOUNDS, A PROCESS FOR ITS PREPARATION AND ITS USE; U.S. Pat. No. 4,975,407; Dec. 4, 1990; relates to a catalyst derived from iron oxides providing agents and potassium oxide providing agents, characterized in that the molar ratio is in the range of from 1.5 to 60 and that a potassium ferrite $K_2Fe_{12}O_{19}$ phase is present supported on an octahedral $Fe_3O_4$ matrix, showing crystalline epitaxy between the hexagonal structure of $K_2Fe_{12}O_{19}$ and the (111) planes of the $Fe_3O_4$ spinel structure.

McFarland, ACETYLENE REMOVAL PROCESS; U.S. Pat. No. 4,658,080; Apr. 14, 1987 relates to a process for removing acetylene from organics streams, particularly those streams resulting from oxidative-dehydrogenation of C4-C8 hydrocarbons, using an acetylene reduction catalyst comprising ferrite and nickel oxide, an alkaline earth metal oxide, carbonate or hydroxide of magnesium, calcium, strontium or barium and an alkaline metal oxide carbonate or hydroxide based on lithium, potassium, sodium, or rubidium. Use of the catalyst is exemplified in a pipe reactor in which oxidative dehydrogenation is conducted on C4-C8 hydrocarbons and the reaction product is immediately passed over a bed of the acetylene reduction catalyst in the same pipe reactor. See also McFarland; ACETYLENE REMOVAL PROCESS; U.S. Pat. No. 4,644,088; Feb. 17, 1987 and U.S. Pat. No. 4,513,159; Apr. 23, 1985.

Patel; PROCESS FOR REMOVING a-ACETYLENES FROM DIOLEFINS; U.S. Pat. No. 4,266,086; relates to removal of alpha-acetylenes including vinyl acetylene and methyl acetylene from a feedstream containing butadiene and mixed monoolefins and alkanes contaminated with alpha-acetylenes in an amount up to about 1.0 percent by weight (% by wt) by contacting the liquid phase with a supported metal oxide catalyst (cupric oxide, silver oxide, or mixtures thereof) in the absence of hydrogen, at a temperature in the range from about 90° C. (200° F.) to about 130° C. (260° F.).

In Besozzi et al.; PURIFICATION OF UNSATURATED COMPOUNDS; U.S. Pat. No. 4,150,063; Apr. 17, 1979; gaseous streams containing unsaturated hydrocarbons and carbonyl compounds are contacted with a catalyst comprising at least one metal of group 8, 1b, 2b, 4b, 6b and at least one element from group 1a and 2a to destroy the carbonyl compounds without substantial loss of unsaturated hydrocarbons.

Miklas, METHOD OF ACTIVATING ZINC-FERRITE OXIDATIVE DEHYDROGENATION CATALYST; U.S. Pat. No. 3,953,370; Apr. 27, 1976 relates to use of steam at a temperature of from 370-700° C. (700-1300° F.) to activate a zinc ferrite oxidative hydrogenation catalyst for preparation of butadiene from $C_4$-$C_8$ hydrocarbons.

Tschopp; DIOLEFIN PRODUCTION AND PURIFICATION; U.S. Pat. No. 3,943,185; Mar. 9, 1976 relates to a process for producing a stream of oxidatively dehydrogenated $C_4$ hydrocarbons substantially free of oxygen and inert noncondensable gases removed comprising absorbing the $C_4$ hydrocarbons in an absorber oil in a first zone; stripping oxygen and inert noncondensable gases from the mixture of adsorber oil and $C_4$ hydrocarbons in a second zone which is operated under conditions of temperature and pressure to maintain an aqueous phase in the second zone; and withdrawing (1) a predominately aqueous phase from the second zone, (2) an overhead of predominately all of the oxygen and inert noncondensable gases and a bottoms of adsorber oil and C4 hydrocarbon substantially free of oxygen and inert noncondensable gases.

In Woerner et al; PURIFICATION OF UNSATURATED HYDROCARBONS BY EXTRACTIVE DISTILLATION WITH ADDITION OF LIQUID SOLVENT TO STRIPPER OVERHEAD; U.S. Pat. No. 3,496,070; Feb. 17, 1970, a hydrocarbon separation process is provided for the separation of a hydrocarbon mixture comprising 4 to 5 carbon atoms including unsaturated hydrocarbons which comprises: extractively distilling the hydrocarbon mixture with a selective solvent in an extractive distillation column whereby hydrocarbon is selectively extracted in the extractive distillation column to form a hydrocarbon-rich solvent fraction which is fed to a solvent stripping column with said solvent being taken off as a bottoms from said stripping column and a vaporous hydrocarbon fraction being taken as an overhead fraction from said stripping column; adding said selective solvent in liquid phase to the vaporous overhead from the solvent stripper to lower the pressure in the overhead condenser of the solvent stripper column and in the solvent stripper. It is said that the product of the process may alternatively be taken as an overhead from the solvent stripper instead of from the extractive distillation column.

Bajars; DEHYDROGENATION WITH MAGNESIUM FERRITE; U.S. Pat. No. 3,284,536; Nov. 8, 1966 relates to dehydrogenating hydrocarbons in the vapor phase at elevated temperatures in the presence of oxygen and a catalyst containing magnesium ferrite. Hydrocarbons to be dehydrogenated according to the process are hydrocarbons of 4 to 7 carbon atoms, preferably aliphatic hydrocarbons selected from the group consisting of saturated hydrocarbons, monoolefins, diolefins and mixtures thereof of 4 to 5 or 6 carbon atoms having a straight chain of at least four carbon atoms, and cycloaliphatic hydrocarbons. Oxygen is present in the reaction zone in an amount within the range of 0.2 to 2.5 mols of oxygen per mol of hydrocarbon to be dehydrogenated. The temperature for the dehydrogenation reaction will be greater than 250° C., such as greater than about 300° C. or 375° C., and the maximum temperature in the reactor may be about 650° C. or 750° C. or perhaps higher under certain circumstances.

Levin et al.; PROCESS FOR REMOVING ALDEHYDES AND/OR KETONES FROM AN OLEFINIC STREAM; US Patent Application Publication 2004/0122275; Jun. 24, 2004 relates to removing an oxygenate impurity selected from aldehyde and/or ketone, from an olefinic product stream. The product stream is contacted with a metal oxide-containing catalyst in the presence of a C1 to C6 alcohol under conditions sufficient to convert the oxygenate impurity to an olefin and/or oxygenate of higher carbon number than the aldehyde and/or ketone. The metal oxide-containing catalyst typically comprises an oxide of at least one metal selected from the group consisting of Group 2 metals, Group 3 metals (including Lanthanide and Actinide series metals), and Group 4 metals. The catalyst may include two or more metals from the same group of metals. In one embodiment, the metal oxide containing catalyst comprises lanthanum oxide and magnesium oxide. In another, the catalyst comprises an oxide of a metal selected from the group consisting of Ti, Zr, and Hf. In yet another embodiment, the catalyst preferably comprises an oxide of a metal selected from the group consisting of Sc, Y, La, and Ce.

Van Egmond; DISTILLATION PROCESS FOR REMOVAL OF METHYL ACETYLENE AND/OR PROPADIENE FROM AN OLEFIN STREAM; US Patent Application Publication 2004/0122268; Jun. 24, 2004 relates to a process for producing a propylene product stream and/or a butylene product stream from an olefin stream by removing Methyl acetylene and/or propadiene (MAPD) from the propylene and/or butylene in a two-step fractionation process.

Welch, et al. in "BUTADIENE VIA OXIDATIVE DEHYDROGENATION", Hydrocarbon Processing November 1978 pp. 131-136; discuss an oxidative dehydrogenation process, in which steam, air or oxygen, and normal butenes are heated and passed over an undisclosed autoregenerative heterogeneous catalyst at around 430° C. (800° F.) using steam as a heat sink to moderate the temperature rise in the adiabatic reactor system without using gas phase additives such as halogen and sulfur compounds. The process is said to consume essentially all of the oxygen in the feed usually leaving oxygen levels in the effluent below 0.3 percent. Acetylenes and oxygenated byproducts are major by products.

SUMMARY OF THE INVENTION

The present invention provides a method of manufacturing butadiene from a butene rich feed, comprising the steps of providing a butene rich hydrocarbonaceous feed, vaporizing and super heating said hydrocarbonaceous butene rich feed to a temperature of at least about 205° C. (400° F.), mixing said hydrocarbonaceous butene rich feed with superheated steam and an oxygen rich gas to form a reactor feed stream, the moles of oxygen in said reactor feed stream being controlled to fall in the range of at least about 0.4, more preferably at least about 0.5 moles of oxygen per mole of hydrocarbonaceous butene rich feed, oxidatively dehydrogenating said reactor feed stream over a catalyst comprising: a major proportion of iron oxide; a minor proportion of zinc oxide; and smaller amounts of manganese oxide; and phosphoric acid, along with a calcium oxide derived from a non-nitrogenous calcium precursor, preferably calcium acetate, and thereby forming a butadiene enriched product stream. In a typical embodiment the heated reaction feed mixture is passed over a multilayer bed comprising four layers: an inert flow distribution and catalyst retention layer, preferably comprising spheres of alpha-alumina, which restricts channeling of the reaction mixture as it passes through the catalyst bed and also serves to hold the lower layers in place against vorticity that might be present above the catalyst bed; the second layer comprising the bulk of the bed being a oxidation/dehydrogenation catalyst having itself a depth of more than 69 or 70 cm (27 inches); while the third layer comprises an aldehyde and alkyne removal ("AAR") catalyst which converts alkynes and aldehydes in the product into compounds which are less detrimental to processes for polymerization of butadienes than alkynes and aldehydes; and the lowest layer comprises an inert particulate support material. Preferably, inlet conditions, primarily temperature are controlled such that the oxidative dehydrogenation reactions initially occur in the lower part of the oxidative dehydrogenation catalyst bed, so that coking is avoided in those portions of the bed above the initial reaction zone and at least 3, preferably at least 5, more preferably at least about 8, up to from about 10 to 75 or more remotely readable thermocouples are inserted into the oxidation/dehydrogenation portion of the bed to monitor the temperature therein at a variety of depths as well as at locations spaced laterally, with respect to the direction of flow, therefrom, and the temperature profile is monitored to determine when the effective portion of the catalyst nearest the AAR catalyst is becoming deactivated. When this occurs, the inlet temperature is increased slightly so that location where the oxidation/dehydrogenation reactions are occurring may be walked up the catalyst bed slightly and a new layer of catalyst is brought into effective use. Subsequently, the reaction process is monitored to determine when the newly employed layer of catalyst is becoming deactivated and the inlet temperature is again increased to move the effective reaction layer higher in the bed. In this fashion, coking of the upper layers of catalyst can be controlled so that a layer of catalyst relatively unaffected by coking is always in use until the uppermost layer in the bed becomes severely enough deactivated that a catalyst change out is justified. Simultaneously through this process, oxygen content in the AAR catalyst as well as the lower layers of the oxidative dehydrogenation catalyst can be monitored as a backup to monitoring the temperature profile to further ensure that oxygen breakthrough into the AAR catalyst and the highly undesirable consequences thereof are avoided.

Suitable ferritic oxide catalysts for the present invention are usually somewhat friable or frangible so that, when conventional techniques are used to formulate and load the catalyst, there is considerable difficulty in ensuring that the catalyst bed does not become partially clogged by catalyst particle fragments. Such fragments can result from loading, relative motion between particles during operation or even the simple weight of particles above once the full depth of the bed has been reached. This issue may be addressed by both (i) pre-reducing the catalyst particles before they are loaded into the reactor to render them more wear resistant; as well as by (ii) loading the catalyst using a low impact loading technique such as sock or even loading the catalyst by hand as opposed to simple dumping. Ideally both the pre-reducing technique and low impact placement techniques will be used together to ensure that the pressure drop through the bed remains as low as possible.

BRIEF DESCRIPTION OF THE DRAWINGS

The invention is described in detail below with reference to numerous examples and the appended Figures wherein like numbers designate similar parts throughout and wherein.

DETAILED DESCRIPTION OF THE PREFERRED EMBODIMENT

The invention is described in detail below in connection with the Figures for purposes of illustration, only. The invention is defined in the appended claims. Terminology used throughout the specification and claims herein are given their ordinary meanings, for example, "indirect heat transfer" refers to heat transfer from one medium to another medium through a heat exchanger wall and pressures refer to gauge pressures unless otherwise indicated. When carrying out the inventive process, preferably heat is transferred through a single heat exchanger wall from a higher temperature stream to a lower temperature stream, such as from reactor effluent to reactor feed in a feed superheater as described hereinafter. Indirect heat transfer may be carried out in accordance with the invention using any suitable equipment such as tube and shell heat exchangers or plate and frame heat exchangers.

Unless otherwise indicated, "butadiene" or "BD" refers to 1,3 butadiene or mixtures comprising 1,3 butadiene.

The front end of butadiene production system of the present invention comprises multiple largely identical process trains, each process train having one reactor 30 producing a butadiene enriched product stream from which useful heat is extracted by indirect heat exchange before entering quench tower 64 at which point all process streams are combined. Only one train will be illustrated to avoid needless over-complication.

Figure 1A:
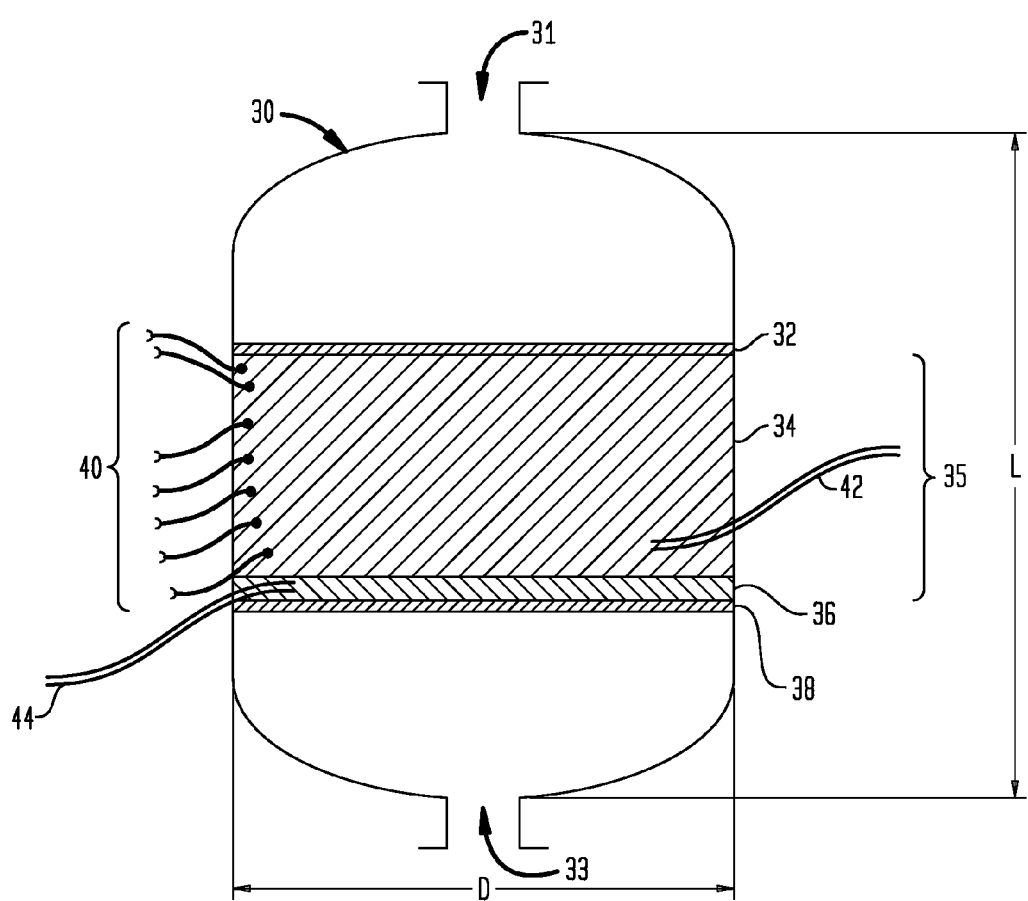
FIG. 1A is a schematic sectional view of a reactor for use the practice of the present invention.
Figure 1B:
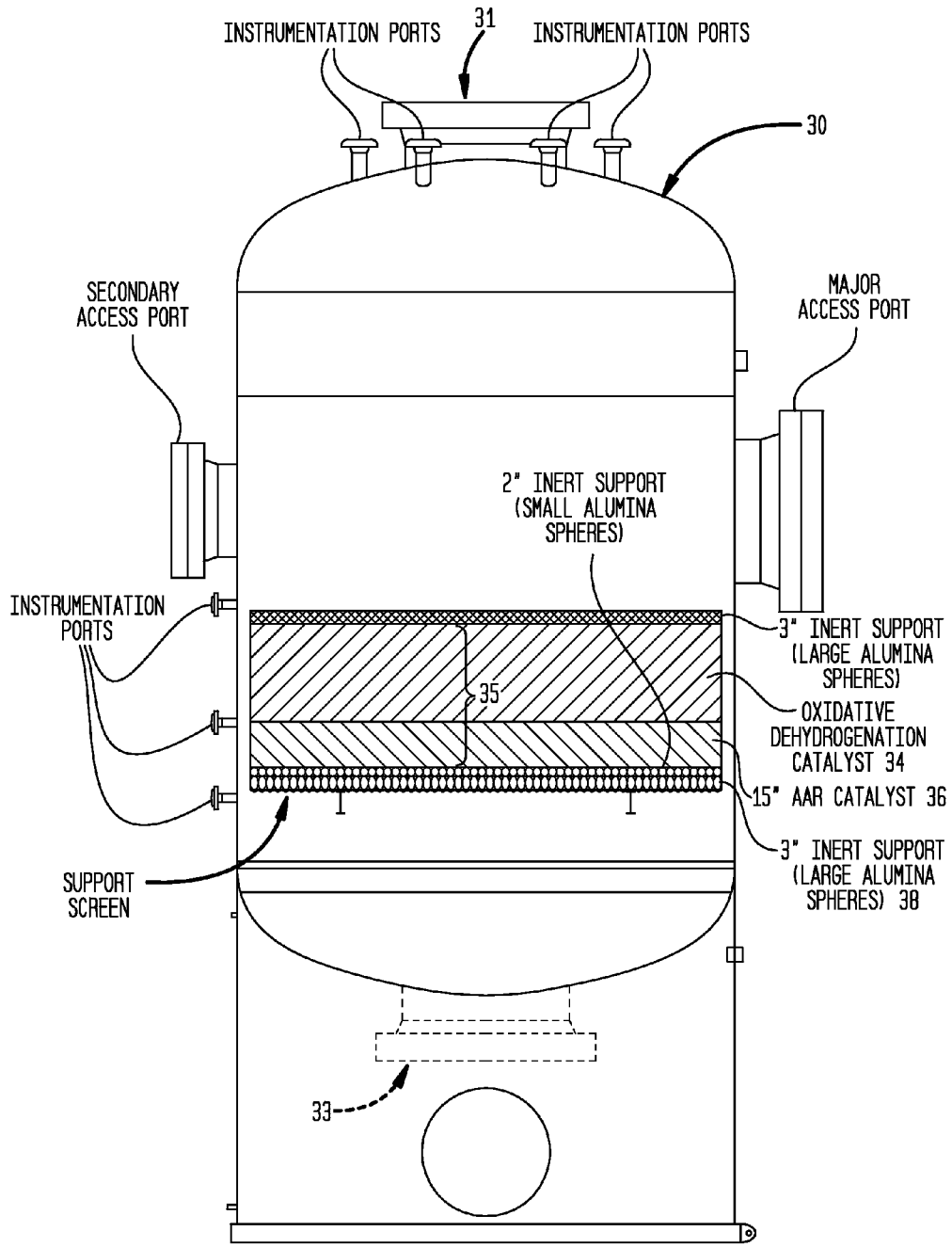
FIGS. 1B and 1C are more detailed schematics of a reactor shell illustrating the overhead space in the reactor above the catalyst support grid as well as the relative disposition of the access and instrumentation ports and the catalyst support grid.
Figure 1C:
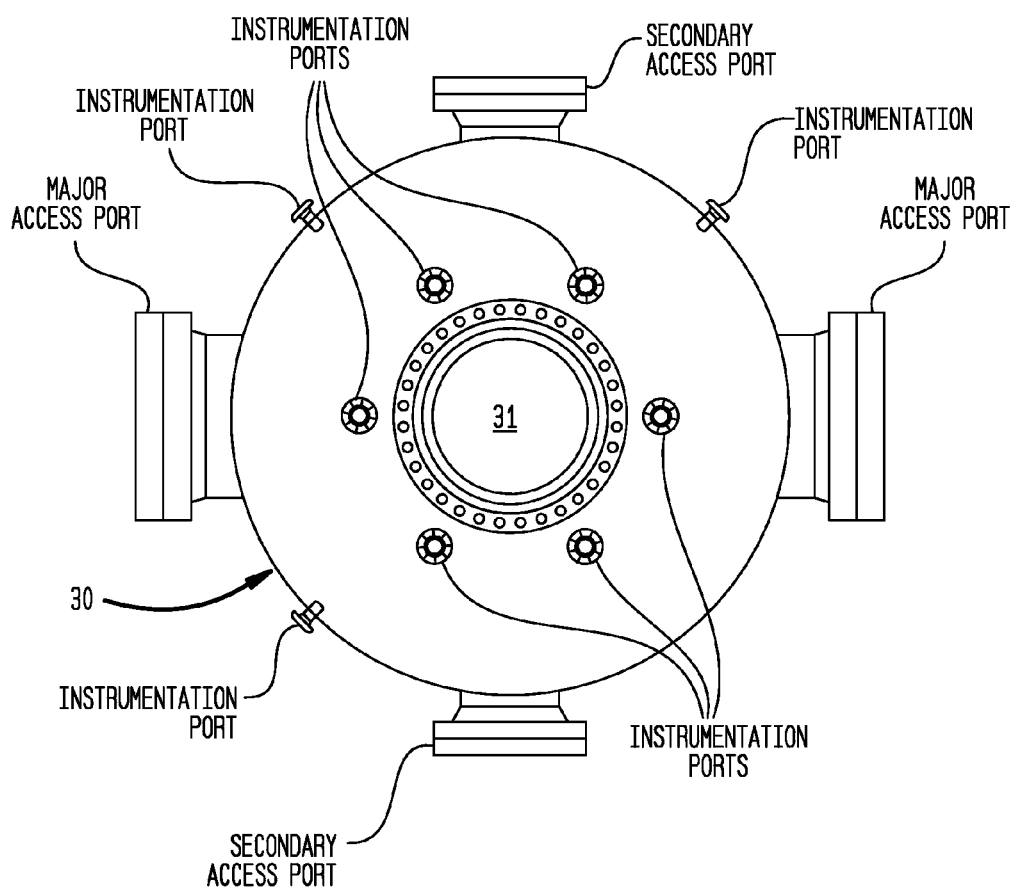

Referring to FIGS. 1A-1C, reaction feed mixture comprising a butene rich hydrocarbonaceous gas, oxygen in a ratio of about 0.55 moles of oxygen per mole of hydrocarbon and steam in a ratio of about 15 moles of steam per mole of hydrocarbon enter reactor 30 through an upper inlet port 31 of reactor 30 and flows downwardly before impacting upon layer 32 of inert granules of alumina having an average particle size of about 3 mm to about 10 mm. Typically, these inert particles will be of a low surface area alumina such as perhaps alpha-alumina rather than some of the higher surface area forms usually loosely referred to as gamma alumina, although there are several intermediate forms of alumna exhibiting higher surface area than alpha-alumina. Spheres of alpha alumina having the following characteristics are quite suitable for both the uppermost and lowest layers in the catalyst bed:

| PROPERTIES | MIN | MAX |
|---|---|---|
| Nominal Diameter, Inches | ¼ | ½ |
| To Pass Opening, Inches | 0.371 | 0.624 |
| To Be Retained On Opening, Inches | 0.263 | 0.525 |
| Bulk Density, lb/cu. ft | 128 | 125 |
| Nominal Diameter, cm | 0.635 | 1.27 |
| To Pass Opening, cm | 0.942 | 1.585 |
| To Be Retained On Opening, cm | 0.668 | 1.334 |
| Bulk Density, kg/m³ | 2050 | 2002 |

Upper layer 32 may be from about 50 mm to about 100 mm in depth, such as from about 65 to 85 mm in depth and in some cases from about 70 to 80 mm. Each layer in the catalyst bed, including upper layer 32, is installed using a low-impact placement such as a sock loading technique to avoid damage to the catalyst layers therebelow while the depth of upper layer 32 is limited to avoid crushing of the oxidative dehydrogenation catalyst therebeneath. When catalyst particles are sock loaded, it is important to avoid subjecting them to large forces such as those resulting from dropping the particles from a significant height. If the height of the sock above the bed is controlled so that particles are not allowed to fall through heights of more than about 91 cm (36 inches), there is little danger of significant damage to the particles, although drops from as high as 185 cm (70-75 inches) can sometimes be tolerated, particularly if the particles have been pre-reduced or otherwise heat treated to improve their toughness. Similarly, when the catalyst is placed in the hopper at the upper end of the sock, care is likewise observed so that the catalyst particles are not dropped from an excessive height. Hand loading can be used as well.

In other configurations, the sections of the bed 35 which includes layers 34, 36 can be arranged as annular sections with the reactants flowing radially through the bed. Ideally the inert flow distribution granules will be sized and configured to prevent disturbance to oxidative dehydrogenation layer 34 underneath due to any turbulence or vorticity in the flow of reaction feed mixture approaching the catalyst bed. The oxidative dehydrogenation catalyst particles can be of any physical arrangement that will provide effective contact between the catalytically active species and the reactants, including dispersed on an inert support, but will typically be massive particles rather than being actives dispersed on a high surface area catalyst support. Preferably, the catalyst particles are from about 1 to about 25-30 mm in size, often taking the form of extrudates or spheres from about 1 mm up to about 5 mm in diameter. In particular, the catalyst particles preferably used in connection with the present invention should be slightly larger than commonly used in previous practice to limit the pressure drop through the catalyst bed as we prefer to use a catalyst bed which is deeper than commonly used previously. Higher pressure drop requires higher pressure in the system which reduces selectivity. We also prefer to use catalyst particles having two key differences from previous practice: (1) the particles are "pre-reduced" or otherwise heat treated prior to loading to give them the crush strength necessary to be usable in a bed having a depth of from about 50 cm to about 150 cm (from about 20" up to about 60"), suitably a depth of from about 65 cm to about 130 cm (from about 25" to about 50"), or from about 75 cm to about 100 cm (from about 30" to about 40"); while the bulk density of the calcined particles is no more than about 1100 kg/m³ (about 70 lbs/ft³), suitably between about 880 kg/m³ and 1050 kg/m³ (about 55 lbs/ft³ and 65 lbs/ft³) or between about 920 kg/m³ and 1010 kg/m³ (about 58 lbs/ft³ and 63 lbs/ft³) and (2) it is preferred to avoid the use of nitrates that are conventionally used as precursors for the calcium compounds often incorporated into these catalysts. Calcium acetate is a suitable precursor in this regard and has the advantage of reducing NOx emissions, while calcium chloride and calcium carbonate are also suitable.

Oxidative dehydrogenation catalyst particles having a composition as set forth in a companion application hereto, LOW EMISSIONS OXIDATIVE DEHYDROGENATION PROCESS FOR PRODUCING BUTADIENE referenced above are disposed in layer or bed 34 having a depth of from over 69 cm (27") up to about 152 cm (60"), preferably between about 71 cm (28") and 127 cm (50"), more preferably between about 76 cm (30") and 102 cm (40"), the butene rich hydrocarbonaceous feed is converted to a butadiene enriched reaction product stream which proceeds downstream of layer or bed 34 of oxidative dehydrogenation catalyst particles though layer or bed 36 of AAR catalyst In layer 36 of AAR catalyst particles, alkynes and aldehydes in butadiene enriched reaction product stream are converted to more innocuous species that are not so detrimental to use of butadiene in usual subsequent polymerization reactions. Preferably, AAR catalyst layer 36 is present in a depth of from about 40% to about 60% of the depth of the oxidative dehydrogenation catalyst, more preferably about 50%. Alternatively, the depth can be from about 30 cm (12 inches) to about 51 cm (20 inches), more preferably from about 33 cm (13 inches) to about 48 cm (19 inches) and most preferably from about 36 cm (14 inches) to about 46 cm (18 inches). Beneath layer 36 of AAR catalyst lies inert support layer 38 comprised of alumina spheres having a diameter of between about 1.0 cm (0.4 inches) and 2.54 cm (one inch), with inert support layer 38 being preferably from about 2.54 cm (1 inch) to about 20 cm (8 inches) in depth, preferably from about 5.08 cm (2 inches) to about 10 cm (4 inches) in depth, more preferably from about 6.4 cm to 8.9 cm (2.5 to 3.5 inches) in depth and even more preferably from about 6.99 cm to 7.62 cm (2.75 to 3 inches). In other cases, a layer of larger beads may be separated from the AAR catalyst by layer of smaller beads as depicted in FIG. 1A. After exiting inert support layer 38, the butadiene enriched product stream exits reactor 30 though the lower exit port 33 for subsequent recovery of the heat value contained therein and concentration of the butadiene content into a crude butadiene stream having a concentration of approximately 50 to 60% butadiene.

Typically, the catalytic process is initiated by raising the temperature of the catalyst bed to about 425° C. (800° F.); adding reactants until conversion is observed, then reducing the inlet temperatures to control the catalyst bed temperature. In most cases, natural gas is used to bring the streams up to temperature; then use of natural gas is sharply curtailed or cut off entirely once conversion is observed. In steady operation, as butene rich feed initially impacts upon the catalyst bed, the inlet conditions are carefully controlled so that most of the conversion of butenes into butadiene occurs in the last several cm of layer 34 of oxidative dehydrogenation catalyst above the AAR catalyst, which initially registers as essentially a step change in temperature recorded by only the lowest of those thermocouples 40 distributed throughout layer 34 of oxidative dehydrogenation catalyst, the thermocouples in the layer of oxidative dehydrogenation catalyst wherein the reaction is occurring. It is extremely important that the reaction is essentially complete before the reactants reach the AAR catalyst. This is primarily controlled by closely observing the temperature profile in the reactor to ensure that the reaction zone is located above the AAR catalyst and moves upwardly as lower layers of the oxidative dehydrogenation catalyst begin losing catalytic activity. As additional insurance, the location of the reaction zone can be verified by measuring the oxygen content just above the lowermost layer of oxidative dehydrogenation catalyst as well as in the AAR catalyst itself, the presence of any amount of oxygen being considered highly detrimental even though oxygen contents as high as 0.3% to 0.5% can be tolerated for short periods of time. As the reaction progresses, oxidative dehydrogenation catalyst in the lowermost portion of layer 34 of oxidative dehydrogenation catalyst becomes deactivated which is indicated by decline in the registered temperature and may be reflected in selectivity or yield measurements as well. When the lower thermocouples in the array begin to register a decline in temperature such that there is any significant risk of oxygen breakthrough to the AAR catalyst, the inlet temperature is increased slightly to move the reaction zone upwardly in the oxidative dehydrogenation catalyst. In this way, coking of catalyst in layers of oxidative dehydrogenation catalyst above the layer in use is avoided. Throughout the process, the oxygen content, or more precisely the lack of significant oxygen content, in the AAR catalyst is carefully monitored to confirm that oxygen is not breaking through into the AAR catalyst layer. When the uppermost layer of oxidative dehydrogenation catalyst becomes deactivated to the extent that catalyst changeout is called for, the process is interrupted and a new catalyst bed is supplied. In many cases, a catalyst life of over 80 days up to about a year can be achieved, although it is not necessarily prudent to attempt to set records without a fair degree of certainty that oxygen breakthrough will be avoided. Typically, the inlet temperature must be increased progressively throughout the run so process economics suffer somewhat toward the end of the run, further discouraging attempts to set endurance records. In the absence of some upset, we expect a minimum of 180 days of catalyst life if the foregoing precautions are strictly observed.

FIGS. 1B and 1C illustrate a configuration for reactor 30 of the present invention wherein access port(s) sized to allow entry is provided in the side wall of reactor 30 with catalyst support grid 38 spaced therebeneath allowing an overhead space suitably at least about 1.8 m (6 feet) of clearance between the fill level of the catalyst bed and the upper surface of the reactor chamber.

Flow distribution is also important for avoiding channeling and hot spots in the catalyst bed. The preferred flow regime is fully turbulent and is enhanced by the presence of the inlet distributor. That is, an inlet distributor is advantageously provided to insure uniform flow distribution through the catalyst bed and prevent channeling and the potential creation of hot spots, which are likely to shorten the catalyst life. One preferred design for this inlet distributor device is in the form of baffles and rings which is mounted in the vapor space above the catalyst bed to promote even distribution of flow and to minimize inlet pressure losses.

Figure 2:
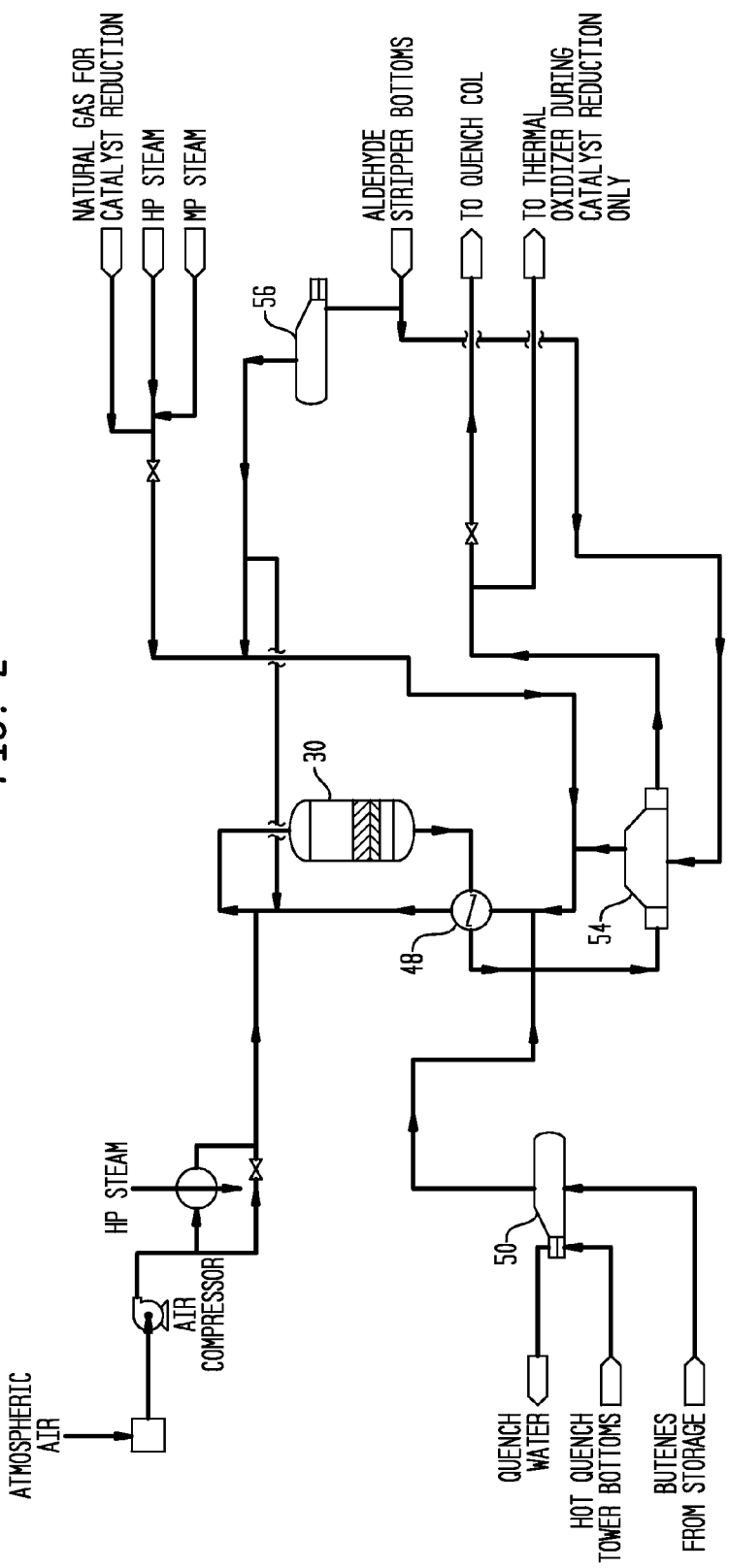
FIG. 2 is a flow diagram of the reactor section of a crude butadiene battery illustrating the reactor and the pretreatment equipment for bringing the butene rich feed to the entry conditions required for operation of the reactor.

Referring to FIG. 2, butene rich feed is vaporized in butene vaporizer 50 in which the heat required for vaporization is supplied by removal of heat from bottoms of quench tower 64 which, as will be discussed later, is heated by contact with the hot reaction product once a steady state operation has been achieve in the current process. After passing through butene vaporizer 50, the vaporized butene feed is mixed with steam, the steam being generated in two recycle condensate vaporizers 54 and 56. The steam generated in recycle condensate vaporizer 54 is produced by indirect heat exchange with butadiene enriched product stream leaving reactor feed superheater 48. The heat required to generate the steam in recycle condensate vaporizer 56 is preferably supplied by steam either from the plant grid or preferably from the thermal oxidizer or some other conveniently available source. Preferably, the steam is completely vaporized in recycle condensate vaporizer 56 prior to being mixed with vaporized butene before passage through reactor feed superheater 48 in which the reactor feed is preheated by indirect heat exchange with the butadiene enriched product stream exiting reactor 30 with the resultant combined entry stream having a temperature of at least about 345° C. (about 650° F.), preferably in the range of from about 345° C. to 400° C. (from about 650° F. to 750° F.). Thus the feed to reactor 30 is heated to the required temperature by indirect heat exchange with the exit stream which, as will be discussed later, is usually at a temperature in excess of 535° C. (1000° F.), more typically around 595° C. (1100° F.). Significantly, the recovered heat passes through only a single tube wall in contrast to schemes in which an intermediate fluid is used. Preheated reactor feed leaving the reactor feed superheater 48 is mixed with compressed oxygen bearing gas, typically air, with the amount of air feed being carefully controlled so that approximately 0.5 to 0.6 moles of oxygen are supplied for each mole of hydrocarbon in the feed passed to the reactors. In some cases, it will be convenient to preheat the oxygen bearing gas to from about 205 to about 235° C. (about 400 to about 450° F.) using high pressure steam. After mixing, the reaction feed stream is passed to refractory lined adiabatic reactor 30 illustrated in FIG. 1, where butene/steam/air feed inside reactor 30 passes first through: an inert flow distribution layer 32 then to an oxidative-dehydrogenation catalyst layer 34, having a depth of 83.8 cm (33 inches) or so; an aldehyde and acetylene removal (AAR) catalyst layer 36 and an inert support (alumina spheres) layer 38.

The location of the intensely exothermic reaction occurring in each reactor is monitored through a number of remotely readable thermocouples 40 spaced along the height of oxidation-dehydrogenation layer 34 so that the location of the reaction zone therein may be determined. The amount of oxygen remaining in the product stream is monitored with oxygen analyzer 42 located near the bottom of layer 34 so that oxygen breakthrough into AAR layer 36 is avoided as discussed hereinafter in more detail. Also provided is a lower sample port 44 for a convergence analyzer in layer 36 so that composition may be monitored at the lower extreme of the reactor. Thermocouples 40 are also optionally disposed in layer 36 to monitor temperature in the AAR zone. Instead of thermocouples, any suitable temperature sensing device may be utilized, such as resistance temperature detectors, or noncontact sensors in a suitable reactor configuration.

In order to control the system, a target temperature for a reaction zone is pre-selected and maintained in the reaction zone. The reaction zone in layer 34 is initially disposed near the bottom of layer 34. The reaction zone or "active" layer of oxydehydrogenation catalyst layer 34 is characterized by a relatively sharp rise in temperature over a relatively short bed depth to the pre-selected target temperature. Generally, the reaction zone is characterized by a temperature rise of from 100° F. to 300° F. (38° C. to 149° C.) over a bed depth change of from 1 to 5 inches (2.5 cm to 13 cm) to the target temperature. More typically, the active layer is characterized by a temperature rise of from 150° F. to 250° F. (83° C. to 139° C.) over a bed depth of from 2 to 4 inches (5 cm to 10 cm). Below the reaction zone in bed 34, there is preferably no additional temperature rise if the system is controlled properly since oxygen is completely or nearly completely depleted in the reaction zone and is no longer present in the system.

Suitable operating target temperatures for the oxydehydrogenation reaction zone are from 1000° F. to 1200° F. (540° C. to 650° C.). When the targeted temperature of the reaction zone begins to fall, the inlet temperature to the reactor is raised and the active zone migrates upwardly in layer 34. One can estimate the time for oxygen breakthrough based on the rate of change of temperatures in the bed which is manifested in the rate of upward migration of the reaction zone and the remaining bed depth above the reaction zone. The estimate of time to breakthrough is based on the temperature readings in the layers above the reaction zone (which are lower than the target temperature for the reaction zone) more so than on the temperatures at or below the reaction zone since the temperatures above the reaction zone are indicative of relatively fresh catalyst available to catalyze the reaction. Thus, if the temporal temperature profile indicates that the reaction zone is migrating upwardly at a rate of 0.5 cm/day and the uppermost thermocouple(s) indicate a fresh catalyst layer of 5 cm, only 10 days of operation remain before oxygen breakthrough, provided that the oxydehydrogentation catalyst exhaustion rate remains relatively constant.

By controlling migration of the reaction zone in the manner described herein, the oxidative dehydrogenation catalyst gives best performance for extended times.

As mentioned previously, the hot reaction product stream from reactor 30 passes through reactor feed superheater 48 (FIG. 2) which supplies a portion of the heat used to bring the feed to reactor 30 up to the requisite operating temperature and thence the reaction product exiting reactor feed superheater 48 passes through steam generator 54 wherein a portion of the sensible heat contained therein is used to vaporize and/or superheat the steam passing to reactor 30.

Figure 3:
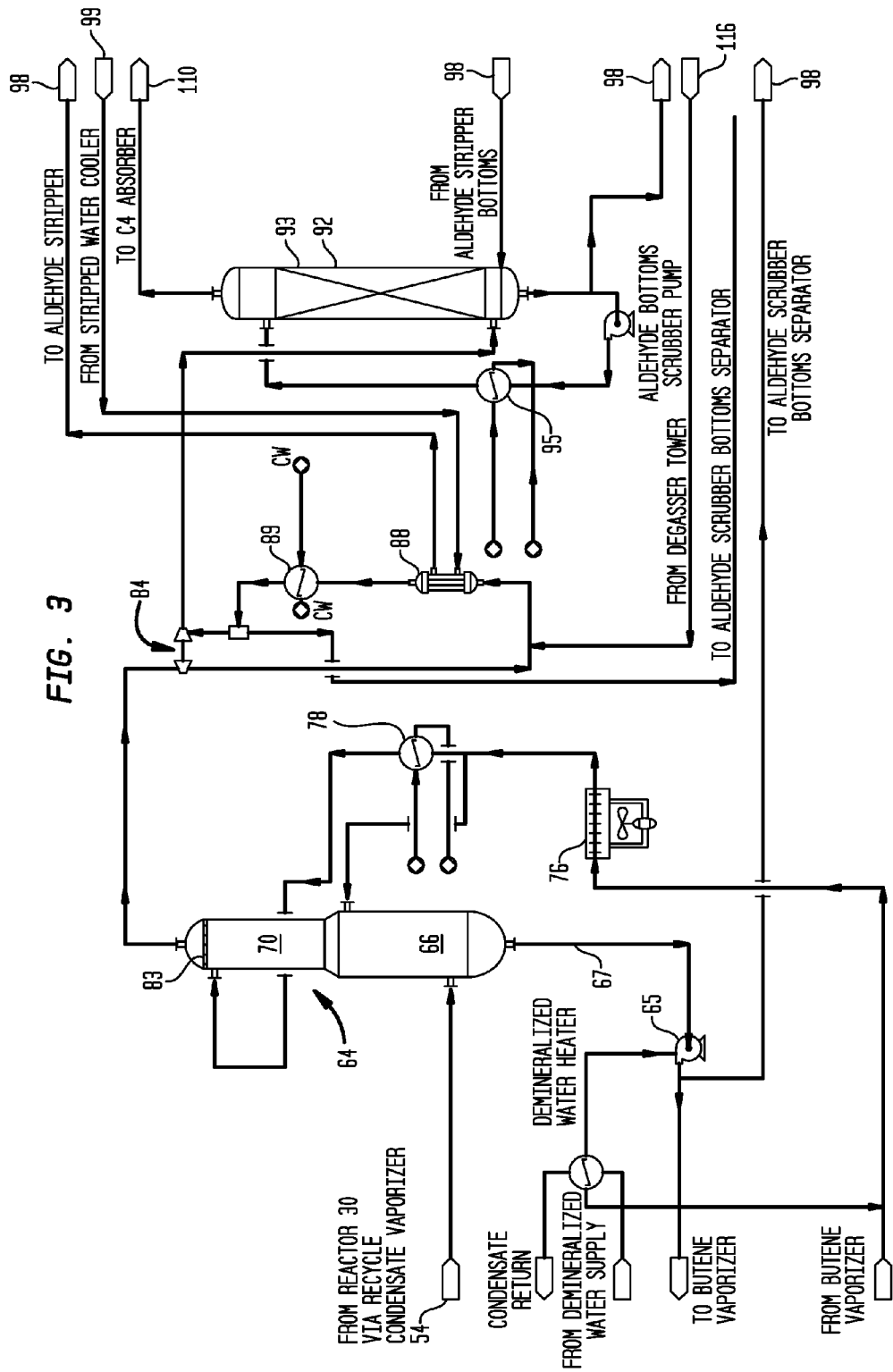
FIG. 3 is a flow diagram of a portion of a crude butadiene battery illustrating the Gas Compressing and Scrubbing equipment for initial processing of a butadiene enriched product stream produced by the reactor section of FIG. 2.

Subsequently, butadiene enriched reaction product exiting from steam generator 54 passes to quench tower 64 (FIG. 3) entering at a height slightly above the maximum liquid level expected during normal operation. As mentioned, in our preferred embodiment, butadiene enriched product stream from reactor 30 is combined with other butadiene enriched product streams from the other reactors (not shown) prior to entering quench tower 64. In one embodiment, bottom section 66 of quench tower 64 is equipped with valve trays while top section 70 is equipped with a corrugated metallic structured packing such as Koch Flexipac®, similar to that described in Lantz, et al., U.S. Pat. No. 6,874,769, Structured Packing Plate and Element and Method of Fabricating Same or Rukovena, U.S. Pat. No. 4,740,334. Alternatively, spray nozzles may be used for the entire tower. It is anticipated that in many cases, it will be possible to feed the mixture of vaporous and liquid reaction product effluent directly into quench tower 64 without any preliminary phase separation; but such preliminary phase separation can be easily accommodated, if expedient, by incorporation of a flash tank or similar phase separation device. The condensate liquid phase collected at lower exit 67 of quench tower 64 composed primarily of condensed steam and quench water is fed back through the hot side of butene vaporizer 50 with cooled liquid return being passed back via quench condensate air cooler 76 and thence to quench tower circulating cooler 78 before being fed into quench tower 64 at a location well above the top of the packed section 70 of quench tower 64 but below demister pad 83. Preferably quench condensate air cooler 76 is equipped with modular tube banks, individually controlled fans, and variable pitch fan blades to facilitate temperature control in a variety of ambient conditions. In many cases, it will be possible to extract additional heat from Quench Tower 64 bottoms stream for uses elsewhere in the associated plant reducing size and cost of Quench Tower Coolers 76 and 78.

Figure 4:
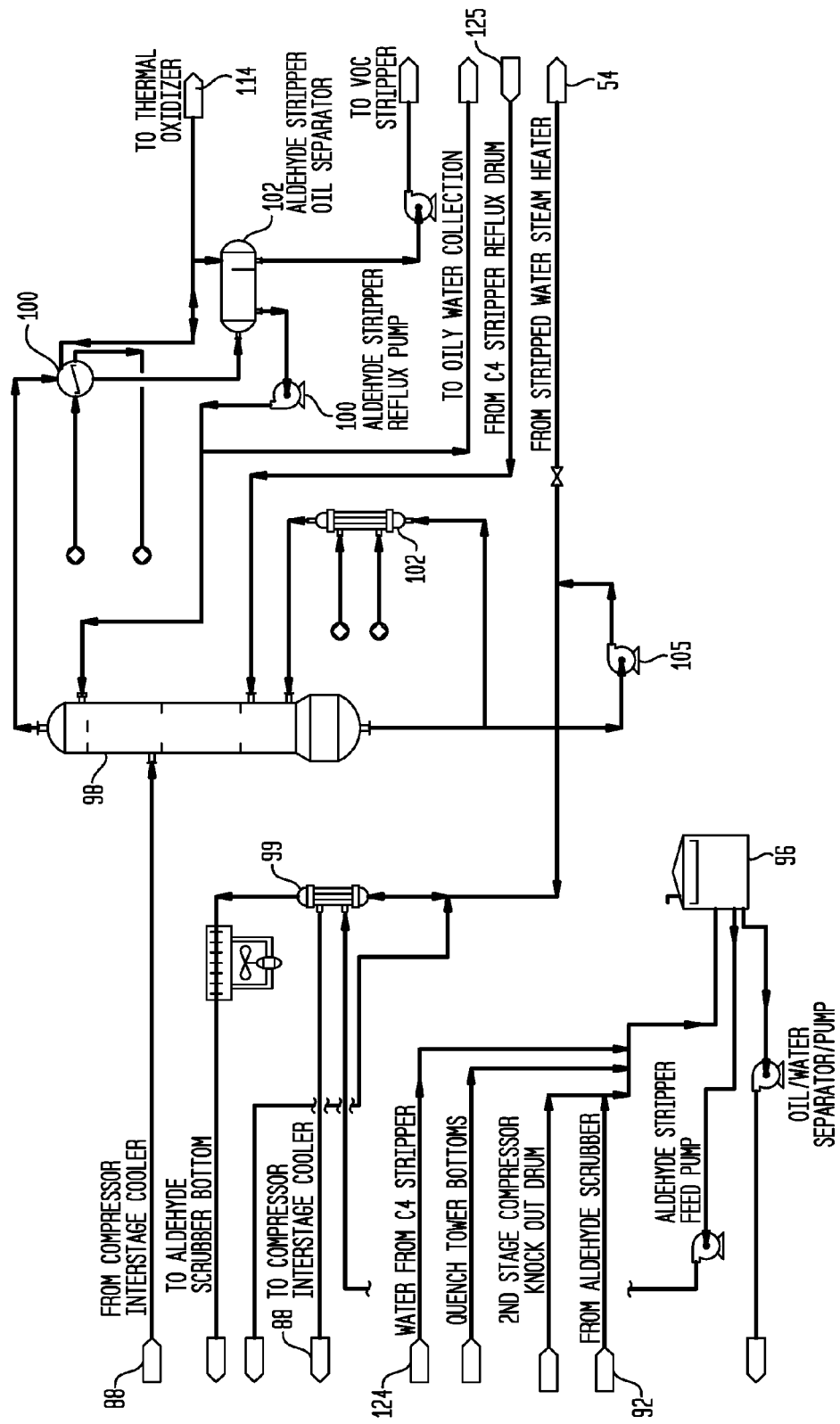
FIG. 4 is a flow diagram of a portion of a crude butadiene battery illustrating the aldehyde stripper and associated equipment for processing a butadiene enriched product stream after processing by the Gas Compressing and Scrubbing section of FIG. 3.

Crude butadiene vapor leaves top section 70 of quench tower 64 (FIG. 3) passing through demister pad 83, which is included primarily to protect gas compressor 84 from any entrained liquid droplets, and enters on the suction side of two-stage centrifugal gas compressor 84. Indirect inter-stage cooling is provided by compressor inter-stage coolers 88 and 89 with cooling to compressor inter-stage cooler 88 being supplied by a process stream leaving stripped water cooler 99 and the heated stream from the shell side of compressor inter-stage cooler 88 being fed to aldehyde stripper 98 (FIG. 4). Cooling to inter-stage cooler 89 is conveniently supplied by plant cooling tower water.

Entrained liquid droplets coalesced on demister pad 83 are refluxed through quench tower 64 while compressed vaporous butadiene enriched product compressed to 1140 kPa abs. (about 150 psig) leaves the second stage of the gas compressor and it is passed to aldehyde scrubber 92 of which top portion 93 is preferably packed with structured packing which may be similar to Norton Intallox structured packing or those packings described above. A portion of the bottoms from aldehyde scrubber 92 is recycled through the structured packing via aldehyde scrubber bottoms cooler 95 while the remainder is passed to aldehyde stripper 98 via aldehyde scrubber bottoms separator 96 (FIG. 4) which receives liquid from the quench tower 64 bottoms via quench tower bottoms pump 65 (FIG. 3) as well as from gas compressor 84 second stage knock out drum. The water contents of the aldehyde scrubber bottoms separator 96 (FIG. 4) may be returned to quench tower 64 at a location below demister pad 83. It is an important aspect of this invention that in those cases where substantial amounts of hydrocarbons lighter than C4 or other low value volatiles can be removed from various streams herein, those off gases are fed to a thermal oxidizer where they are combusted to produce steam which can be used to supply heat as needed for various portions of the overall process thereby greatly reducing need for natural gas combustion in steady operation and thereby also reducing concomitant generation of carbon monoxide and carbon dioxide.

Aldehyde stripper (FIG. 4) receives the water phase from the aldehyde scrubber bottoms after the oil phase has been skimmed out. This stream is pumped first to the shell side of stripped water cooler 99, from whence it reaches the shell side of compressor interstage cooler 88, which helps to increase its temperature via heat integration before being fed to aldehyde stripper 98, a portion of this overhead vapor from aldehyde stripper 98 going to aldehyde stripper overhead condenser 100 and thence being returned to aldehyde stripper 98 as reflux to maintain the vapor/liquid equilibrium in the column and drive overhead the aldehydes contained in the feed to this tower 98. The balance of the overhead vapor stream from aldehyde stripper 98 bypassing overhead condenser 100 is combined with other low value combustibles and directed to a thermal oxidizer (not shown) for production of superheated steam. Heavier hydrocarbons entrained in the condensed overhead stream from overhead condenser 100 are collected by bottoms coalescer and are also disposed of by treatment at a conventional oily water facility (not shown). Aldehyde stripper reboiler 102 uses steam, advantageously medium pressure steam, to vaporize a portion of aldehyde stripper bottoms from aldehyde stripper 98 and reintroduces the vapor below bottom tray of aldehyde stripper 98 while the remainder is pumped using adehyde stripper bottoms pump 105 to two locations: (1) back to the aldehyde scrubber 92 bottoms below the packing via two stripped water coolers (not shown), and (2) to the recycle condensate vaporizers, where it generates the vast bulk, if not all, of the steam used for the oxidative dehydrogenation reaction.

Figure 5:
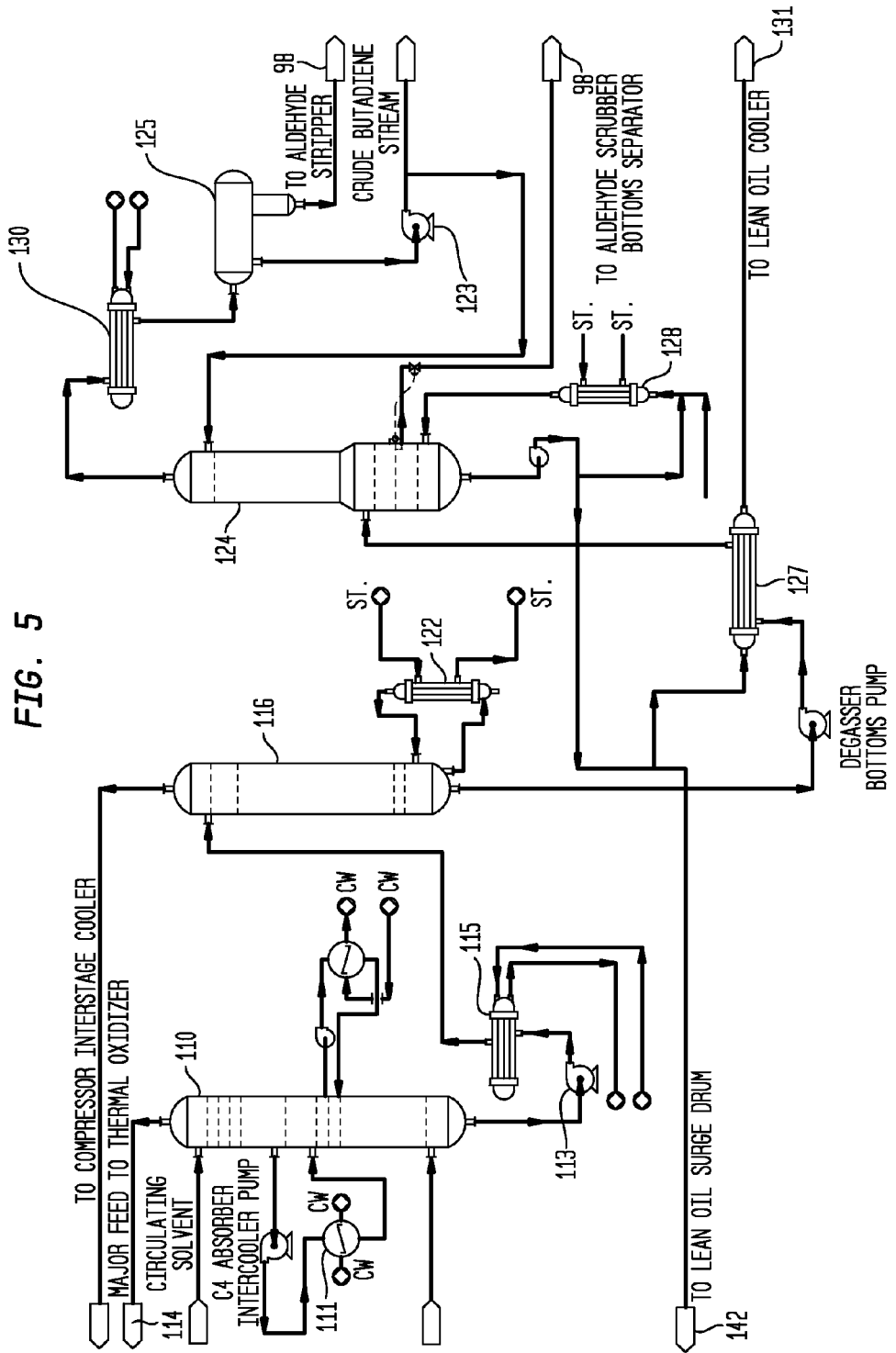
FIG. 5 is a flow diagram of a portion of a crude butadiene battery illustrating the C4 absorption and stripping equipment for production of a crude stream of about 50% butadiene by processing of a butadiene enriched product stream received from the aldehyde stripper section of FIG. 4.

Reaction product from aldehyde scrubber 92 (FIG. 3) overhead is passed to the bottom of C4 absorber 110 (FIG. 5) containing numerous trays or other known devices for promoting gas liquid contact and equipped with at least one intercooler 111. Absorber oil (also sometimes referred to as lean oil) used in absorber 110 can suitably be paraffinic, or a mixture of paraffins and aromatics, although particularly superior results are obtained using oils which are richer in, or possibly even entirely, vinyl cyclohexene (butadiene dimer). Good commercial results have been obtained when the fresh absorber oil is primarily Espersol 250, an aromatic Naphtha product with a boiling range of 90° C. to 150° C. (200° F. to 300° F.) having the composition shown in Table 1 (Celsius Boiling Points provided in Table 1A). Alternatively, a paraffinic naptha product with similar boiling points may be used.

TABLE 1

Absorber Oil Composition

| Component | Molecular Weight | N.B. Point (° F.) | Specific Gravity | Chroma. % | Assumed Wt % | Mole % | Vol. % |
|---|---|---|---|---|---|---|---|
| Benzene | 78.11 | 176.2 | 0.8845 | 6 | 5 | 6.8 | 5 |
| Cyclohexane | 84.16 | 178 | 0.783 | 3 | 2 | 2.5 | 2.3 |
| Methyl Cyclohexane | 98.18 | 213.7 | 0.774 | 1 | 1 | 1.1 | 1.1 |
| Toluene | 92.13 | 231 | 0.872 | 12 | 13 | 15 | 13.2 |
| 2,2,4-Trimethyl Pentane | 114.23 | 236.1 | 0.696 | 1 | 2 | 1.9 | 2.6 |
| Vinyl Cyclohexane | 108.18 | 262.1 | 0.8335 | 3 | 5 | 4.9 | 5.3 |
| Ethyl Cyclohexane | 112.22 | 269.2 | 0.788 | 1 | 1 | 0.9 | 1.1 |
| M&P-Xylene | 106.16 | 281 | 0.867 | 19 | 20 | 20.1 | 20.4 |
| O-Xylene | 106.16 | 291 | 0.885 | 17 | 18 | 18.1 | 18 |
| Styrene | 104.14 | 294 | 0.911 | 10 | 12 | 12.3 | 11.6 |
| Propyl Benzene | 120.19 | 318.6 | 0.862 | 1 | 2 | 1.8 | 2.1 |
| Butyl Benzene | 134.21 | 361.4 | 0.864 | 4 | 6 | 4.8 | 6.1 |
| "Heavies" (Assume 2-M Naphthalene) | 142.2 | 466 | 1.029 | 22 | 13 | 9.7 | 11.2 |

TABLE 1A

Absorber Oil Composition (Celsius Boiling Points)

| Component | Molecular Weight | N.B. Point (° C.) | Specific Gravity | Chroma. % | Assumed Wt % | Mole % | Vol. % |
|---|---|---|---|---|---|---|---|
| Benzene | 78.11 | 80.11 | 0.8845 | 6 | 5 | 6.8 | 5 |
| Cyclohexane | 84.16 | 81.1 | 0.783 | 3 | 2 | 2.5 | 2.3 |
| Methyl Cyclohexane | 98.18 | 100.9 | 0.774 | 1 | 1 | 1.1 | 1.1 |
| Toluene | 92.13 | 111 | 0.872 | 12 | 13 | 15 | 13.2 |
| 2,2,4-Trimethyl Pentane | 114.23 | 113.4 | 0.696 | 1 | 2 | 1.9 | 2.6 |
| Vinyl Cyclohexane | 108.18 | 127.8 | 0.8335 | 3 | 5 | 4.9 | 5.3 |
| Ethyl Cyclohexane | 112.22 | 131.8 | 0.788 | 1 | 1 | 0.9 | 1.1 |
| M&P-Xylene | 106.16 | 138 | 0.867 | 19 | 20 | 20.1 | 20.4 |
| O-Xylene | 106.16 | 144 | 0.885 | 17 | 18 | 18.1 | 18 |
| Styrene | 104.14 | 146 | 0.911 | 10 | 12 | 12.3 | 11.6 |
| Propyl Benzene | 120.19 | 159.2 | 0.862 | 1 | 2 | 1.8 | 2.1 |
| Butyl Benzene | 134.21 | 183 | 0.864 | 4 | 6 | 4.8 | 6.1 |
| "Heavies" (Assume 2-M Naphthalene) | 142.2 | 241 | 1.029 | 22 | 13 | 9.7 | 11.2 |

Butadiene in the product stream is absorbed in absorber oil introduced at the top of C4 absorber 110, the bottoms from which is pumped to the top of degasser tower 116 through C4 absorber bottoms pump 113 and degasser feed cooler 115. Degasser tower 116 operates at lower pressure to facilitate the removal of residual gases, particularly carbon dioxide, nitrogen and hydrogen, which are passed through inter-stage cooler 88 of two-stage gas compressor 84 to the butadiene enriched product stream prior to passage through aldehyde scrubber 92. Degasser overhead gas from degasser 116 is recycled back to the second stage of compressor 84 and thence to scrubber 92 and absorber 110 whence it will ultimately find its way to thermal oxidizer 114. Degasser reboiler 122 maintains the temperature in the liquid phase of degasser tower 116 sufficiently high to allow residual gases to be flashed out passing to thermal oxidizer 114 as described above. The bottoms from degasser tower 116 largely comprising crude butadiene and miscellaneous C4's in absorber oil are passed to C4 stripper 124 through C4 stripper feed bottoms interchanger 127 where this bottoms stream is heated by passage of hot absorber oil from the bottoms of C4 stripper 124 through the tubes of C4 stripper feed/bottoms interchanger 127. Heated degasser bottoms are introduced into C4 stripper 124 at an intermediate height. Crude butadiene and C4's are stripped from heated absorber oil in C4 stripper 124, passing out as overhead to C4 stripper overhead condenser 130 while depleted absorber oil collected in the bottoms from C4 stripper 124 is reheated in C4 stripper reboiler 128; and the overhead vapor from C4 stripper 124 is condensed in C4 stripper overhead condenser 130 with a portion of the condensed liquid being accumulated in C4 stripper reflux drum 125, where residual water can be separated from the hydrocarbon phase and sent back to aldehyde stripper tower 98, while crude butadiene product is pumped through C4 stripper reflux pump 123 to further processing, while sufficient crude butadiene is being recirculated as reflux to ensure that sufficient separation is attained in C4 stripper 124.

Figure 6:
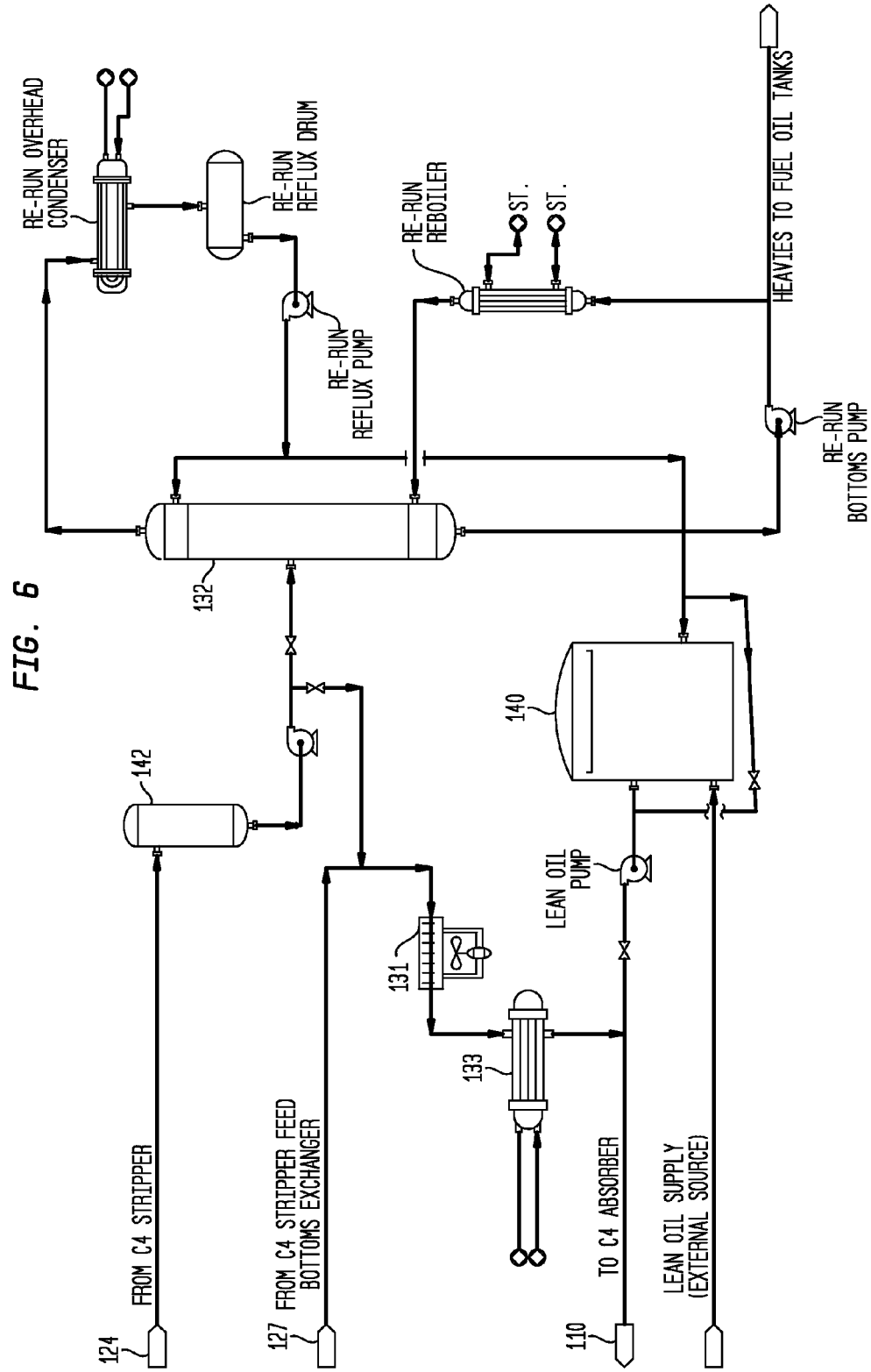
FIG. 6 is a flow diagram of a portion of a crude butadiene battery illustrating portions of the system used for handling of lean oil after stripping of C4's therefrom.

Bottoms leaving C4 stripper 124 comprise absorber oil having butadiene and other C4s stripped therefrom which is divided into three portions, one of which is recirculated to C4 stripper 124 through C4 stripper reboiler 128, a second portion being passed to absorber oil surge drum 142, (FIG. 6) the remaining portion being used as mentioned previously to heat butadiene/absorption oil mixture upon passage through C4 stripper feed/bottoms interchanger 127 where it, and oil being recycled from absorption oil surge drum 142, are passed to absorption oil air cooler 131 and absorption oil cooler 133 before being returned to C4 absorber 110 for reuse. As absorber oil breaks down, forming heavier molecules, fresh oil make-up is introduced into the system while the balance is directed to a re-run column for heavies cleanup. Upon sufficient accumulation of heavies in the absorption oil to justify, or necessitate, operation of absorber oil re-run tower 132, a portion of the oil being recirculated from absorption oil surge drum 142 is distilled to remove heavier components in absorber oil re-run tower bottoms with the overhead being pumped back to absorber oil recirculation loop. Occasionally the recovered oil could be pumped to storage tank 140 (FIG. 6) where the fresh absorber oil is stored.

Tables 2 and 2A sets forth an energy balance for three possible plant configurations for 23,000 kg/hr (50,600 lb/hr) of butadiene production: one having no thermal oxidizer; one having a small thermal oxidizer sized primarily for the low value combustibles produced in the process of converting butene to butadiene; and one sized for both the low value combustibles produced in the process of converting butene to butadiene as well as those produced in the process of purifying crude butadiene to a saleable grade. It can be appreciated that the energy requirement for vaporizing and superheating the various streams fed to the reactor during steady operation of the process for converting butenes to butadiene is surprisingly small when sensible heat in the reaction product stream is combined with the energy resulting from thermal oxidation of low value combustibles from both butadiene production and purification.

TABLE 2

Low Emissions/Heat Integration for Oxidative Dehydrogenation of Butene

| | |
|---|---|
| BD Production: | 50,600 LB/HR |
| Total Energy† Required: | 432,112,000 BTU/HR |

Energy provided by Sensible Heat in Butadiene Enriched Product Stream (BTU/HR)

| | |
|---|---|
| Butene Vaporizer 50 | 14,558,000 |
| Superheater 48 (Butene) | — |
| Superheater 48 (Steam) | 95,783,000 |
| Condensate Vaporizer 54 | 111,613,000 |
| SubTotal† | 221,954,000 |

Additional Energy Required to Vaporize Steam for Reactor Feed (BTU/HR) *

| | |
|---|---|
| Condensate Vaporizer 56 | 210,159,000 |

| Thermal Oxidizer Size: | Energy Contribution from Combustion of By-Products (Supplied via Steam) | % Energy from Process Sources | % Energy from Fossil fuel | Lbs. of NG required for each lb of Butadiene Produced | % Energy for Vaporizing Recycle Condensate and Superheating Feed from Thermal Oxidizer | % Energy for Vaporizing Recycle Condensate and Superheating Feed from Reactor Effluent |
|---|---|---|---|---|---|---|
| none | 0 | 51 | 48 | 0.20 | — | 51 |
| offgases from Crude BD production only | 150,000 #/hr 150# Steam | 61 | 39 | 0.16 | 10 | 51 |

TABLE 2-continued

Low Emissions/Heat Integration for Oxidative Dehydrogenation of Butene

| | | | | | | |
|---|---|---|---|---|---|---|
| Offgases from production and purification of Crude BD | 250,000 #/hr 150# Steam | 91 | 9 | 0.04 | 40 | 51 |

* Energy calculated based on 150# superheated steam @ 810° F. generated by combination of thermal oxidation of by-products from butene and butadiene production as supplemented by combustion of natural gas at 21,000 BTU/LB as fuel for steam boiler to produce 1112 BTU/LB of Steam during first phase of steady operation
†Totals do not agree perfectly due to rounding.

TABLE 2A (Metric Units)
Low Emissions/Heat Integration for Oxidative Dehydrogenation of Butene

| | |
|---|---|
| BD Production: | 23,000 kg/HR |
| Total Energy† Required: | 455,597,000 kJ/HR |

Energy provided by Sensible Heat in Butadiene Enriched Product Stream (kJ/HR)

| | |
|---|---|
| Butene Vaporizer 50 | 15,349,000 |
| Superheater 48 (Butene) | — |
| Superheater 48 (Steam) | 100,988,000 |
| Condensate Vaporizer 54 | 117,679,100 |
| SubTotal† | 234,017,000 |

Additional Energy Required to Vaporize Steam for Reactor Feed (kJ/HR) *

| | |
|---|---|
| Condensate Vaporizer 56 | 221,581,000 |

| Thermal Oxidizer Size: | Energy Contribution from Combustion of By-Products (Supplied via Steam) | % Energy from Process Sources | % Energy from Fossil fuel | kg. of NG required for each kg of Butadiene Produced | % Energy for Vaporizing Recycle Condensate and Superheating Feed from Thermal Oxidizer | % Energy for Vaporizing Recycle Condensate and Superheating Feed from Reactor Effluent |
|---|---|---|---|---|---|---|
| none | 0 | 51 | 48 | 0.20 | — | 51 |
| offgases from Crude BD production only | 68,000 kg/hr 1 MPa Steam | 61 | 39 | 0.16 | 10 | 51 |
| Offgases from production and purification of Crude BD | 113,000 kg/hr 1 MPa Steam | 91 | 9 | 0.04 | 40 | 51 |

* Energy calculated based on 68.0 kg superheated steam @ 432° C. generated by combination of thermal oxidation of by-products from butene and butadiene production as supplemented by combustion of natural gas at 48,813 kJ/kg as fuel for steam boiler to produce 2585 kJ/kg of Steam during first phase of steady operation Energy requirements for the reaction section can also be expressed in kJ/kg (BTU/LB) BD (butadiene) produced as set forth in Tables 3 and 3A below.

TABLE 3

Reaction Section Energy Utilization

| | | |
|---|---|---|
| Total Energy required*: | 8540 | BTU/LB BD |
| Energy for Superheater 48 | 1890 | BTU/LB BD |
| Energy for Vaporizer 50 | 288 | BTU/LB BD |
| Energy for Vaporizer 54 | 2200 | BTU/LB BD |
| Energy for Vaporizer 56 | 4150 | BTU/LB BD |

*Approx. values

TABLE 3A

Metric Units

| | | |
|---|---|---|
| Total Energy required*: | 19,900 | kJ/kg BD |
| Energy for Superheater 48 | 4,400 | kJ/kg BD |
| Energy for Vaporizer 50 | 670 | kJ/kg BD |
| Energy for Vaporizer 54 | 5,130 | kJ/kg BD |
| Energy for Vaporizer 56 | 9,650 | kJ/kg BD |

*Approx. values

All of the energy for Superheater 48, over 4400 kJ/kg (1900 BTU per pound) of butadiene, may be supplied by indirect heat transfer of sensible heat from the reactor effluent stream at high temperature, with the effluent product stream well above 370° C. (700° F.). Likewise, all of the energy for vaporizer 54 may similarly be supplied by indirect heat transfer at a somewhat lower temperature of the effluent product stream. Heat recovery from the process stream is enhanced by extracting heat from the effluent stream when the stream is at a relatively high temperature for purposes of superheating the feed and then extracting heat from the reactor effluent at a relatively lower temperature for purposes of vaporizing feed. Energy for vaporizer 56 may be supplied from a plant steam grid which draws heat from thermal oxidation of volatile organic compounds generated in connection with the oxidative dehydration process as described herein.

In its various aspects, the inventive method may be practiced using a ferritic oxidative dehydrogenation catalyst which is substantially nitrate-free and may comprise: oxygen, a major proportion of iron; a minor proportion of zinc; and smaller amounts of manganese; phosphorus and a residue of a nitrate free calcium precursor. So also, the process may be operated wherein the moles of oxygen in said reactor feed stream are controlled to so that at least 0.5 moles of oxygen are provided per mole of hydrocarbonaceous butene rich feed. The ferritic oxidative dehydrogenation catalyst bed generally has a depth of over 70 cm (27 inches) and the temperature sensing devices comprise thermocouples.

In one preferred embodiment, there is provided a method of manufacturing butadiene from a butene rich feed, comprising the steps of:

providing a catalyst bed layer of granules of ferritic oxidative dehydrogenation catalyst and a bed of particles of AAR catalyst therebeneath, said catalyst bed of ferritic oxidative dehydrogenation catalyst having a plurality of thermocouples embedded therein through its depth including at least one thermocouple spaced from about 5 to about 10 cm above the layer of AAR catalyst and another located from about 15 to about 25 cm above the layer of AAR catalyst;

providing a butene rich hydrocarbonaceous feed, vaporizing and super heating said hydrocarbonaceous butene rich feed to a temperature of at least about 345° C. (650° F.), mixing said hydrocarbonaceous butene rich feed with superheated steam and an oxygen rich gas to form a reactor feed stream;

controlling inlet conditions to said reactor such that the oxidative dehydrogenation reactions occur in the lower most layers of said oxidative dehydrogenation catalyst, including in a reaction zone, reacting said reactor feed stream over said catalyst and thereby forming a butadiene enriched product stream;

monitoring the temperature throughout the bed and from time to time in response to a drop in the temperature in the reaction zone, calculating from time to time when oxygen breakthrough should occur based upon the measured temperatures and based upon the observed rate of change in the temperatures indicated by the plurality of thermocouples;

increasing the inlet temperature when the active layer of oxidative dehydrogenation catalyst begins to become deactivated so that the reaction zone moves upwardly in the oxidative dehydrogenation bed, calculating from time to time when oxygen breakthrough should occur based upon the measured temperatures and based upon the observed rate of change in the temperatures indicated by the plurality of thermocouples and discontinuing the feed of butene rich hydrocarbonaceous feed before the predicted time for oxygen breakthrough, wherein during at least some period of time, the predicted time calculated for oxygen breakthrough is based upon the temperatures indicated by at least two thermocouples nearer the uppermost oxidative dehydrogenation catalyst layer more so than the temperatures indicated by thermocouples more distantly spaced from the uppermost oxidative dehydrogenation catalyst layer; and discontinuing the feed of butene rich hydrocarbonaceous feed prior to the anticipated time of oxygen breakthrough as indicated by the temperature profile in the oxidative dehydrogenation catalyst bed.

The oxidative dehydrogenation catalysts may range from about 1 mm to about 30 mm in diameter such as from about 1 mm up to about 5 mm in diameter, optionally wherein the particles are pre-reduced or otherwise heat treated prior to loading to a degree sufficient to give them a crush strength necessary to be usable in a bed having a depth of from about 70 cm (27") up to about 150 cm (60"), the bulk density of the pre-reduced particles being no more than about 1120 kg/m$^3$ (70 lbs/ft$^3$). The bulk density of the pre-reduced particles may be between about 930 kg/m$^3$ and 1010 kg/m$^3$ (58 lbs/ft$^3$ and 63 lbs/ft$^3$). Suitably, wherein the oxidative dehydrogenation catalysts comprise: oxygen, a major proportion of iron; a minor proportion of zinc; and smaller amounts of manganese; phosphorus and a residue of a nitrate free calcium precursor.

In another aspect of the invention, a method of manufacturing butadiene from a butene rich feed, comprises the steps of:

providing a catalyst bed layer of granules of ferritic oxidative dehydrogenation catalyst and a bed of particles of AAR catalyst therebeneath by positioning said catalyst particles in said bed by positively positioning, without dumping, said particles, said catalyst bed of ferritic oxidative dehydrogenation catalyst having a plurality of thermocouples embedded therein through its depth including at least one thermocouple spaced from about 5 to about 10 cm above the layer of AAR catalyst and another located from about 15 to about 25 cm above the layer of AAR catalyst;

providing a butene rich hydrocarbonaceous feed, vaporizing and super heating said hydrocarbonaceous butene rich feed to a temperature of at least about 345° C. (650° F.), mixing said hydrocarbonaceous butene rich feed with superheated steam and an oxygen rich gas to form a reactor feed stream;

controlling inlet conditions to said reactor such that the oxidative dehydrogenation reactions occur in the lower most layers of said oxidative dehydrogenation catalyst, including in a reaction zone, reacting said reactor feed stream over said catalyst and thereby forming a butadiene enriched product stream;

monitoring the temperature throughout the bed and from time to time in response to a drop in the temperature in the reaction zone, calculating from time to time when oxygen breakthrough should occur based upon the measured temperatures based upon the observed rate of change in the temperatures indicated by the plurality of thermocouples;

increasing the inlet temperature when the active layer of oxidative dehydrogenation catalyst begins to become deactivated so that the reaction zone moves upwardly in the oxidative dehydrogenation bed, calculating from time to time when oxygen breakthrough should occur based upon the measured temperatures and based upon the observed rate of change in the temperatures indicated by the plurality of thermocouples and discontinuing the feed of butene rich hydrocarbonaceous feed before the predicted time for oxygen breakthrough, wherein during at least some period of time, the predicted time calculated for oxygen breakthrough is based upon the temperatures indicated by at least two thermocouples nearer the uppermost oxidative dehydrogenation catalyst layer more so than the temperatures indicated by thermocouples more distantly spaced from the uppermost oxidative dehydrogenation catalyst layer; and discontinuing the feed of butene rich hydrocarbonaceous feed prior to the anticipated time of oxygen breakthrough as indicated by the temperature profile in the oxidative dehydrogenation catalyst bed.

In still yet another aspect of the invention there is provided a method of manufacturing butadiene from a butene rich feed, comprising the steps of:

providing a catalyst bed of granules of ferritic oxidative dehydrogenation catalyst and a bed of particles of AAR catalyst therebeneath, said catalyst bed of ferritic oxidative dehydrogenation catalyst having a plurality of at least about 5 thermocouples embedded therein through its depth including at least one thermocouple spaced from about 5 to about 10 cm above the layer of AAR catalyst and another located from about 15 to about 25 cm above the layer of AAR catalyst, providing a butene rich hydrocarbonaceous feed, vaporizing and super heating said hydrocarbonaceous butene rich feed to a temperature of at least about 345° C. (650° F.), mixing said hydrocarbonaceous butene rich feed with superheated steam and an oxygen rich gas to form a reactor feed stream;

controlling inlet conditions to said reactor such that the oxidative dehydrogenation reactions occur in the lower most layers of said oxidative dehydrogenation catalyst, including in a reaction zone, reacting said reactor feed stream over said catalyst and thereby forming a butadiene enriched product stream;

monitoring the temperature throughout the bed and from time to time in response to a drop in the temperature in the reaction zone, active layer, calculating from time to time when oxygen breakthrough should occur based upon the measured temperatures based upon the observed rate of change in the temperatures indicated by the plurality of thermocouples, increasing the inlet temperature when the active layer of oxidative dehydrogenation catalyst begins to become deactivated so that the reaction zone moves upwardly in the oxidative dehydrogenation bed, and discontinuing the feed of butene rich hydrocarbonaceous feed before the predicted time for oxygen breakthrough.

In any embodiment, the oxidative dehydrogenation catalyst may comprise: oxygen, a major proportion of iron; a minor proportion of zinc; and smaller amounts of manganese; phosphorus and a residue of a nitrate free calcium precursor.

A particularly preferred embodiment is directed to a method of manufacturing butadiene from a butene rich feed, comprising the steps of:

providing a butene rich hydrocarbonaceous feed, vaporizing and super heating said hydrocarbonaceous butene rich feed to a temperature of at least about 650° F., mixing said hydrocarbonaceous butene rich feed with superheated steam and an oxygen rich gas to form a reactor feed stream, the moles of oxygen in said reactor feed stream being controlled to fall in the range of at least about 0.5 moles of oxygen per mole of hydrocarbonaceous butene rich feed;

providing a catalyst bed having a depth of over about 70 cm (27 inches) of granules of substantially nitrate-free ferritic oxidative dehydrogenation catalyst, passing said reactor feed stream through said catalyst bed and thereby forming a butadiene enriched product stream;

providing a bed of particles of AAR catalyst therebeneath, said catalyst beds having a plurality of thermocouples embedded therein through the depth of each bed including at least one thermocouple spaced from about 5 to about 10 cm above the layer of AAR catalyst and another located from about 15 to about 25 cm above the layer of AAR catalyst, controlling inlet conditions to said reactor such that the oxidative dehydrogenation reactions initially occur in the lower most layers of said oxidative dehydrogenation catalyst, including in a reaction zone, reacting said reactor feed stream over said catalyst and thereby forming a butadiene enriched product stream;

monitoring the temperature throughout the bed and from time to time in response to a drop in the temperature in the reaction zone, increasing the inlet temperature when the active layer of oxidative dehydrogenation catalyst begins to become deactivated so that the reaction zone moves upwardly in the oxidative dehydrogenation bed, and discontinuing the feed of butene rich hydrocarbonaceous feed after the temperature indicated by the thermocouple located in the uppermost portions of the oxidative dehydrogenation catalyst bed begins to drop.

While the invention has been described in detail, modifications within the spirit and scope of the invention will be readily apparent to those of skill in the art. In view of the foregoing discussion, relevant knowledge in the art and references including co-pending applications discussed above in connection with the Background and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

As our invention, we claim:

1. A method of manufacturing butadiene from a butene rich feed, comprising the steps of:
   providing a butene rich hydrocarbonaceous feed, vaporizing said butene rich hydrocarbonaceous feed, mixing said vaporized butene rich hydrocarbonaceous feed with steam to produce a combined stream and superheating the combined stream to provide a reactor feed stream at a temperature of at least about 345° C.;
   providing a catalyst bed comprising layers of granules of oxidative dehydrogenation catalyst in a reactor having an inlet, passing said reactor feed stream and an oxygen rich gas from the inlet through said catalyst bed and thereby forming a butadiene enriched product stream via oxidative dehydrogenation reactions, wherein said catalyst bed of oxidative dehydrogenation catalyst has associated therewith a plurality of temperature sensing devices adapted to measure temperature in the catalyst bed along a direction of flow;
   controlling inlet conditions to said reactor such that most of the oxidative dehydrogenation reactions initially occur in a reaction zone located in the layer of said oxidative dehydrogenation catalyst bed most distal to said inlet, said reaction zone being characterized by an operating target temperature, wherein said inlet conditions include an inlet temperature; and
   monitoring the temperature along the length of the oxidative dehydrogenation catalyst bed and from time to time in response to a drop in the temperature in the reaction zone, increasing the inlet temperature so that the reaction zone migrates toward said inlet through said oxidative dehydrogenation catalyst bed, wherein at any location of the reaction zone within the oxidative dehydrogenation catalyst bed, the reaction zone is characterized by said operating target temperature.

2. The method of manufacturing butadiene from a butene rich feed of claim 1, further comprising passing the butadiene enriched product stream through a bed of AAR catalyst effective to remove acetylenic impurities therefrom.

3. The method of manufacturing butadiene from a butene rich feed of claim 1, wherein the granules of oxidative dehydrogenation catalyst range from about 1 mm to about 30 mm in diameter.

4. The method of manufacturing butadiene from a butene rich feed of claim 1, wherein the granules of oxidative dehydrogenation catalyst range from about 1 mm up to about 5 mm in diameter.

5. The method of manufacturing butadiene from a butene rich feed of claim 1, wherein the oxidative dehydrogenation catalyst is a ferritic oxidative dehydrogenation catalyst.

6. The method of manufacturing butadiene from a butene rich feed of claim 5, wherein the ferritic oxidative dehydrogenation catalyst is substantially nitrate-free.

7. The method of manufacturing butadiene from a butene rich feed of claim 6, wherein the ferritic oxidative dehydrogenation catalyst comprises: oxygen, iron; zinc; manganese; phosphorus and a residue of a nitrate-free calcium precursor.

8. The method of manufacturing butadiene from a butene rich feed of claim 1, wherein the moles of oxygen in said oxygen rich gas are controlled so that at least 0.5 moles of oxygen are provided per mole of butene in said butene rich hydrocarbonaceous feed.

9. The method of manufacturing butadiene from a butene rich feed of claim 1, wherein the catalyst bed has a depth of over 70 cm.

10. The method of manufacturing butadiene from a butene rich feed of claim 1, wherein the temperature sensing devices comprise thermocouples.

11. A method of manufacturing butadiene from a butene rich feed, comprising the steps of:
providing a butene rich hydrocarbonaceous feed, vaporizing said butene rich hydrocarbonaceous feed, mixing said vaporized butene rich hydrocarbonaceous feed with steam to produce a combined stream and superheating the combined stream to provide a reactor feed stream at a temperature of at least about 345° C.;
providing a catalyst bed comprising layers of granules of ferritic oxidative dehydrogenation catalyst in a reactor having an inlet, passing said reactor feed stream and an oxygen rich gas from the inlet through said catalyst bed and thereby forming a butadiene enriched product stream via oxidative dehydrogenation reactions;
providing a bed layer of particles of AAR catalyst beneath said catalyst bed of ferritic oxidative dehydrogenation catalyst, wherein
said catalyst bed of ferritic oxidative dehydrogenation catalyst has a plurality of temperature sensing devices embedded therein through its depth including at least one temperature sensing device spaced from about 5 to about 10 cm above the bed layer of AAR catalyst and another located from about 15 to about 25 cm above the bed layer of AAR catalyst;
controlling inlet conditions to said reactor such that most of the oxidative dehydrogenation reactions initially occur in a reaction zone located in the layer of said ferritic oxidative dehydrogenation catalyst bed most distal to said inlet, said reaction zone being characterized by an operating target temperature, wherein said inlet conditions include an inlet temperature; and
monitoring the temperature throughout the ferritic oxidative dehydrogenation catalyst bed and from time to time in response to a drop in the temperature of the reaction zone, increasing the inlet temperature so that the reaction zone migrates toward said inlet through said ferritic oxidative dehydrogenation catalyst bed, wherein at any location of the reaction zone within the ferritic oxidative dehydrogenation catalyst bed, the reaction zone is characterized by said operating target temperature and wherein when the reaction zone is located in a layer of said ferritic oxidative dehydrogenation catalyst bed containing the temperature sensing device located closest to said inlet, and discontinuing the feed of said reactor feed stream through said catalyst bed after the temperature indicated by the temperature sensing device located closest to said inlet begins to drop.

12. The method of manufacturing butadiene from a butene rich feed of claim 11, wherein the granules of ferritic oxidative dehydrogenation catalyst are pre-reduced or otherwise heat treated prior to said providing said catalyst bed to a degree sufficient to give them a crush strength necessary to be usable in a bed having a depth of from about 70 cm up to about 150 cm, the bulk density of the pre-reduced or otherwise heat treated granules being no more than about 1121 kg/m$^3$ (70 lbs/ft$^3$).

13. The method of manufacturing butadiene from a butene rich feed of claim 12, wherein the bulk density of the pre-reduced or otherwise heat treated granules is between about 930 kg/m$^3$ and 1010 kg/m$^3$.

14. The method of manufacturing butadiene from a butene rich feed of claim 11, wherein the ferritic oxidative dehydrogenation catalyst is substantially nitrate-free.

15. The method of manufacturing butadiene from a butene rich feed of claim 14, wherein the ferritic oxidative dehydrogenation catalyst comprises: oxygen, iron; zinc; manganese; phosphorus and a residue of a nitrate-free calcium precursor.

16. The method of manufacturing butadiene from a butene rich feed of claim 11, wherein the moles of oxygen in said oxygen rich gas are controlled so that at least 0.5 moles of oxygen are provided per mole of butene in said butene rich hydrocarbonaceous feed.

17. The method of manufacturing butadiene from a butene rich feed of claim 11, wherein the temperature sensing devices comprise thermocouples.

18. A method of manufacturing butadiene from a butene rich feed, comprising the steps of:
providing a butene rich hydrocarbonaceous feed, vaporizing said butene rich hydrocarbonaceous feed, mixing said vaporized butene rich hydrocarbonaceous feed with steam to produce a combined stream and superheating the combined stream to provide a reactor feed stream;
providing a catalyst bed comprising layers of granules of oxidative dehydrogenation catalyst in a reactor having an inlet, passing said reactor feed stream and an oxygen rich gas from the inlet through said catalyst bed and thereby forming a butadiene enriched product; stream via oxidative dehydrogenation reactions, wherein said catalyst bed of oxidative dehydrogenation catalyst has associated therewith a plurality of temperature sensing devices adapted to measure temperature in the catalyst bed along a direction of flow;
controlling inlet conditions to said reactor such that most of the oxidative dehydrogenation reactions initially occur in a reaction zone located in the layer of said oxidative dehydrogenation catalyst bed most distal to said inlet, said reaction zone being characterized by an operating target temperature, wherein said inlet conditions include an inlet temperature; and
monitoring the temperature along the length of the oxidative dehydrogenation catalyst bed and from time to time in response to a drop in the temperature of the reaction zone, increasing the inlet temperature so that the reaction zone migrates toward said inlet through said oxidative dehydrogenation catalyst bed, and wherein at any location of the reaction zone within the oxidative dehydrogenation catalyst bed, the reaction zone is characterized by (1) said operating target temperature and (2) a temperature rise of at least 38° C. to 149° C. over a bed depth change of from 2.5 cm to 13 cm.

19. A method of manufacturing butadiene from a butene rich feed, comprising the steps of:
providing a butene rich hydrocarbonaceous feed, vaporizing said butene rich hydrocarbonaceous feed, mixing said vaporized butene rich hydrocarbonaceous feed with steam to produce a combined stream and superheating the combined stream to provide a reactor feed stream at a temperature of at least about 345° C.;
providing a catalyst bed comprising layers of granules of oxidative dehydrogenation catalyst disposed in an adiabatic reactor having an inlet;
passing said reactor feed stream and an oxygen rich gas from the inlet through said catalyst bed in said adiabatic reactor and thereby forming a butadiene enriched product stream via oxidative dehydrogenation reactions, wherein said
catalyst bed of oxidative dehydrogenation catalyst has associated therewith a plurality of temperature sensing devices adapted to measure temperature in the catalyst bed along a direction of flow;
controlling inlet conditions to said adiabatic reactor such that most of the oxidative dehydrogenation reactions initially occur in a reaction zone located in the layer of said oxidative dehydrogenation catalyst bed most distal to said inlet, said reaction zone being characterized by an operating target temperature, wherein said inlet conditions include an inlet temperature; and
monitoring the temperature along the length of the oxidative dehydrogenation catalyst bed and from time to time in response to a drop in the temperature of the reaction zone, increasing the inlet temperature so that the reaction zone migrates toward said inlet through said oxidative dehydrogenation catalyst bed, and wherein at any location of the reaction zone within the oxidative dehydrogenation catalyst bed, the reaction zone is characterized by said operating target temperature.

20. The method of manufacturing butadiene from a butene rich feed of claim 1, wherein the operating target temperature of the reaction zone is within the range of from 540° C. to 650° C.

* * * * *